(12) United States Patent
Wittrup et al.

(10) Patent No.: US 8,394,924 B2
(45) Date of Patent: Mar. 12, 2013

(54) DIRECTED ENGAGEMENT OF ACTIVATING FC RECEPTORS

(75) Inventors: K. Dane Wittrup, Chestnut Hill, MA (US); Shanshan Wu Howland, Singapore (SG)

(73) Assignee: Massachusetts Institute of Technology, Cambridge, MA (US)

( * ) Notice: Subject to any disclaimer, the term of this patent is extended or adjusted under 35 U.S.C. 154(b) by 285 days.

(21) Appl. No.: 12/605,273

(22) Filed: Oct. 23, 2009

(65) Prior Publication Data

US 2010/0221248 A1    Sep. 2, 2010

Related U.S. Application Data

(60) Provisional application No. 61/108,011, filed on Oct. 23, 2008.

(51) Int. Cl.
| | |
|---|---|
| *C07K 14/00* | (2006.01) |
| *C07K 16/00* | (2006.01) |
| *C12P 21/08* | (2006.01) |
| *A61K 38/39* | (2006.01) |
| *A61K 39/00* | (2006.01) |

(52) U.S. Cl. .......... 530/350; 530/387.1; 530/387.7; 530/388.1; 530/388.8; 514/9.3; 424/178.1

(58) Field of Classification Search .......... None
See application file for complete search history.

(56) References Cited

U.S. PATENT DOCUMENTS

| | | | |
|---|---|---|---|
| 2003/0105000 A1* | 6/2003 | Pero et al. ................ 514/12 |
| 2004/0123343 A1 | 6/2004 | La Rosa et al. |
| 2004/0241817 A1 | 12/2004 | Umana et al. |
| 2005/0038229 A1 | 2/2005 | Lipovsek et al. |
| 2007/0148126 A1 | 6/2007 | Chen et al. |
| 2007/0161081 A1 | 7/2007 | Jin et al. |
| 2008/0050371 A1 | 2/2008 | Johnson et al. |
| 2008/0248026 A1 | 10/2008 | He et al. |
| 2009/0299040 A1* | 12/2009 | Camphausen et al. ........ 530/395 |

OTHER PUBLICATIONS

Nakamura et al. (Multichain Immune Recognition Receptor Signaling: From Spatiotemporal Organization to Human Disease, Sigalov, AB, ed. Lanes Bioscience and Springer Science +Business Media, 2008. Ch. 17, pp. 220-233).*
Rudikoff et al. (PNAS USA, 1982, 79: 1979-1983).*
Coleman et al. (Research in Immunology, 1994; 145(1): 33-36).*
Burgess et al. (J of Cell Bio. 111:2129-2138, 1990).*
Skolnick et al. (TIBTECH 18:34-39, 2000).*
Ibragimova and Eade (Biophysical Journal, Oct. 1999, vol. 77, pp. 2191-2198).*
Taylor et al. (Clinical Can. Res. Sep. 4, 2007, 13:5133-5143), "Taylor".*
Gussow et al. (1991, Methods in Enzymology 203:99-121).*
Janeway et al. (Immunobiology 5, 2001, p. 100-101).*
International Search Report of the International Searching Authority in Re: PCT/US2009/061963; Date of Mailing Jun. 23, 2010.
UniProtKB/TrEMBL Entry Q3UZF9_MOUSE. Fn1 (Sep. 2, 2008). [Retrieved from the Internet May 24, 2010: http://www.uniprot.org/uniprot/Q3UZF9.txt?version=28>]; amino acids 115-215.
PIR-PSD Entry A29355. fibronectin—chicken (fragment) (Jul. 9, 2004) [Retrieved from the Internet May 24, 2010: http://pir.georgetown.edu/cgi-bin/nbrfget?uid=A29355>]; amino acids 180-280.
Supplementary European Search Report for European Application No. EP 09 82 2818; mailed Oct. 26, 2012.
De Lorenzo, C. et al., "A human, compact, fully functional anti-ErbB2 antibody as a novel antitumor agent," *British Journal of Cancer*, 91(6): 1200-1204 (2004), XP55018747.
Koide, A. and S. Koide, "Monobodies: Antibody Mimics Based on the Scaffold of the Fibronectin Type III Domain," *Methods in Molecular Biology*, 352: 95-109 (Jan. 1, 2007), XP009102789.
McCall, A.M. et al., "Isolation and characterization of an anti-CD16 single-chain Fv fragment and construction of an anti-HER2/neu/anti-CD16 bispecific scFv that triggers CD16—dependent tumor cytolysis," *Molecular Immunology*, 36: 433-445 (Jan. 1, 1999), XP002123159.
Parker, M.H. et al., "Antibody mimics based on human fibronectin type three domain engineered for thermostability and high-affinity binding to vascular endothelial growth factor receptor two," *Protein Engineering, Design & Selection*, 18(9): 435-444 (2005), XP002457979.
Xu, L. et al., "Directed Evolution of High-Affinity Antibody Mimics Using mRNA Display," *Chemistry & Biology*, 9(8): 933-942 (Aug. 2002), XP027353363.

* cited by examiner

*Primary Examiner* — Peter J Reddig
(74) *Attorney, Agent, or Firm* — Hamilton, Brook, Smith & Reynolds, P.C.

(57) ABSTRACT

The present invention features engineered proteins that include a first polypeptide that specifically binds a first target (e.g., a cellular target, such as a cell-surface antigen) and a second polypeptide that selectively binds an activating FcR.

28 Claims, 2 Drawing Sheets

Figure 2: Amino acid sequence alignments of Fn3 mutants with wild type Fn3

```
                        10         20         30         40         50         60         70         80         90        100
                        |          |          |          |          |          |          |          |          |          |
SID NO: 1   VSDVPRDLEVVAATPTSLLISWDAPAVTVRYYRITYGETGGNSPVQEFTVPGSKSTATISGLKPGVDYTITVYAVTGRGDSPASSKPISINYRTEIDKPSQ
SID NO: 6   VSDVSRDLEVVAATPTSLLISWCHHHHRD-YYRITYGETGGNSPVQEFTVPALCPGATISGLKPGVGYTITVYAVTVGEDV----WSISINYTEIDKPEQ
SID NO: 7   VSDVSRDLEVVAATPTSLLISWCHHHHRD-YYRITYGETGGNSPVQEFTVPALCPGATISGLKPGVGYTITVYAVTVGEDV----WSISINYTEIDKPEQ
SID NO: 8   VSDVPRDLEVVAATPTSLLISWMDKEL---YYRITYGETGGNSPVQEFTVPGLS-ATISALKPGVDYTITVYAVTVYDM------PISTNYRAEIDEPSQ
SID NO: 9   VSDVSGDLEVVAATPTSLLISWAMDVAL--YYRIFYGETGGNSPVQEFTVPGLS-TTISALKPGVDYTITVYAVTVGEDV------PISINYRBEIDEPSQ
SID NO:10   VSDVSGDLEVVAATPTSLLISWCHHHHRD-YYRITYGETGGNSPVQEFTVPALCPGATISGLKPGVGYTITVYAVTGEDV-----NPISINYTAEIDEPSQ
SID NO:11   VSDVSGDLEVVAATPTSLLISWCHHHHWD-YYRITYGETGGNSPVQEFTVPALCPGATISGLKPGVGYTITAYAVTVGGDD-----WSISINYTEIDEPSQ
SID NO:12   VSDVSGDLEVVAATPTSLLISWCHHHHRD-YYRITYGETGGNSPVQEFTVPALCPGATISGLKPGVGYTITVYAVTVGEDV-----WSLSINYTEIDEPSQ
SID NO:13   VSDVSRDLEVVAATPTSLLISWCHHHHRD-YYRITYGETGGNSPVQEFTVPALCPGATISGLKPGVGYTITVYAVTVGEDV-----WSISINYTEIDEPSQ
SID NO:14   VSDVSRDLEVVAATPTSLLISWCHHHHRD-YYRITYGETGGNSPVQEFTVPALCPGATISGLKPGVGYTITVYAVTVGEDV-----WSISINYTEIDEPSQ
SID NO:15   VSDAPRDLEVVAETPTSLLISWAMDGAI--YYRITYGETGGNSPVQEFTVPGLS-ATISALKPGVDYTITVYAVTLYDM-------PISINYRDEIDEPSQ
SID NO:16   VSDVPRDLEVVAATPTSLLISWCHHHDPESNS-YYRITYGETGGNSPVQEFTVPGTDSHATISGLKPGVDYTITVYAVTSSG-SN--SMPISINYRTEIDKPSQ
SID NO:17   VSDVPRGLEVVAATPTSLLISWNDMPESDS-YYRITYGETGGNSPVQEFTVPGTDSHATISGLKPGVDYTITVYAVTSSGSN---SMPISINYRTEIDKPSQ
SID NO:18   VSDVSRGLEVVAATPTSLLISWNDMPESDS-YYRITYGETGGNSPVQEFTVPGTDSHATISGLKPGVDYTITVYAVTSSGCSN---SMPISINYRTEINKPSQ
SID NO:19   VTDVPRDLEVVAATPTSLLISWNDMPESDS-YYRITYGETGGNSPVQEFTVPGTDSHATISGLKPGVDYTITVYAVTSSGCSN---SMPISINYRTWAEIDKPSQ
SID NO:20   VSDVPRDLEVVAATPTSLLISWNDMPESDS-YYRITYGETGGNSPVQEFTVPGTDSHATISGLKPGVDYTITVYAVTSSGCSN---SMPMSINYRTEIDKPSQ
SID NO:21   VSDVPRDLEVVAATPTSLLISWNDMPFSDS-YYRITYGETGGNSPVQEFTVPGTDSHATISGLKPGVDYTITVYAVTSSCSN---SMPWSINYRTEIDKPSR
SID NO:22   VSDVPRDLEVVAATPTSLLISWNDMPFSDS-YYRITYGETGGNSPVQEFTVPGTDSHATISGLKPGVDYTITVYAVTSCSN----SMPISINYRTEIDKPSQ
SID NO:23   VSDVPRDLEVVAATPTSLLISWNDMPFSDS-YYRITYGETGGNSPVQEFTVPGTDSHATWSGLKPGVDYTITVYAVASGSN----SMPISINYRTEIDKPSQ
SID NO:24   VSDVPRDLEVVAATPTSLLISWNDMPFSDS-YYRITYGETGGNSPVQEFTVPGTDSHATISGLKPGVDYTITVYAVTSNG-----LVPISINYRTEID----
SID NO:25   VSDVPRDLEVVAATPTSLLISWNDMPFSDS-YYRITYGETGGNSPVQEFTVPGTDSHATISGLKPGVDYTITVYAVTSSG-----SNSMPISINYRTEADKPSQ
SID NO:26   VSDVPRGLEVVAATPTSLLISWEDMPFSDS-YYRITYGETGGNSPVQEFTVPGTMPGHATISGLKPGVDYTITVYAVTSSG-----SNSMPISINSRTEIDKPSQ
SID NO:27   VSDVPRGLEVVAATPTSLLISWNDMPESDS-YYRITYGETGGNSPVQEFTVPGTDSHATISGLKPGVDYTITVYAVTSSG-----SNSMPISINYRTEIDKPSQ
SID NO:28   VSDVPRGLEVVAATPTSLLISWNDMPFSDS-YYRITYGETGGSSPVQEFTVPAGPGHATISGLKPGVDYTITVYAVTSSG-----FNSMPISINYRTEIDKPSQ
SID NO:29   VSDVPRGLEVVAATPTSLLISWNDMPFSDS-YYRITYGETGGNSPVQEFTVPGTESHATISGLKPGVDYTITVYAVTSSG-----SNSMPISINYRTEIDKPSQ
SID NO:30   VSDVPRDLEVVAATPTSLLISWNDMPFSDS-YYRITYGETGGNSPVQEFTVPGHDSHATISGLKPGVDYTITVYAVTSSG-----SNSYPISINYRTEIDKPSQ
SID NO:31   VSDVPRGLEVVAATPTSLLISWNDMPFSDS-YYRIAYGETGGNSPVQEFTVPGHDSHATISGLKPGVDYTITVYAVTSSG-----SNSMPISINYRTEIDKPSQ
SID NO:32   VSDVPRGLEVVMAAAPTSLLINWDMPFSDS-YYRITYGETGGNSPVQEFTVPGHDSHATISGIKPGVDYTITVYAVASSG-----SSKMPISINYRTEIDKPSQ
SID NO:33   VSDVPRGLEVVAATPTSLLINWDMPFSDS--YYRITYGETGGNSPVQEFTVPGHDSHATISGLKPGVDYTITVYAVTSSG-----SSSMPISINYRTEIDKPPQ
SID NO:34   VSDVPRDLEVVMATPTSLLINWDMPFSDS--YYRITYGETGGNSPVQEFTVPAPGHDSHATISGLKPGVDYTITVYAVTSSG----SNSMPISINYRTEIDKPPQ
SID NO:35   VSDVPRDLEVVWATPTSLLINWDMPFSDS--YYRITYGETGGNSPVQEFTVPGHDSHATISGLKPGVDYTITVYAVTSSG-----SNSMPISINYRTEIDKPPQ
```

DIRECTED ENGAGEMENT OF ACTIVATING FC RECEPTORS

CROSS-REFERENCE TO RELATED APPLICATIONS

This application claims the benefit of the filing date of U.S. Provisional Application No. 61/108,011, which was filed on Oct. 23, 2008. For the purpose of any U.S. application that may claim the benefit of U.S. Provisional Application No. 61/108,011, the contents of this earlier filed application are hereby incorporated by reference in their entirety.

FEDERALLY SPONSORED RESEARCH OR DEVELOPMENT

This invention was made with government support under AI065824 awarded by the National Institutes of Health. The government has certain rights in this invention.

INCORPORATION BY REFERENCE OF MATERIAL IN ASCII TEXT FILE

This application incorporates by reference the Sequence Listing contained in the following ASCII text file in its entirety: File name: 00502196002SequenceListing.txt; created on Oct. 17, 2012, 32.3 KB in size.

TECHNICAL FIELD

This invention relates to engineered proteins, and more particularly to proteins that include at least two distinct polypeptides, one of which specifically binds a cellular target and one of which selectively binds an activating Fc receptor.

BACKGROUND

Tumor cells express a variety of gene products that provoke innate and adaptive immune recognition, and the formation of clinically evident tumors can indicate a failure of host defense. One mechanism that facilitates tumor progression is insufficient tumor antigen presentation. The therapeutic effects of many antibodies used to treat cancer have been found to arise from the recruitment of immune effector cells by engaging Fc receptors (Nimmerjahn and Ravetch, Curr. Opin. Immunol. 19:239-245, 2007). Cancer remains a major cause of human morbidity and mortality, and there is a continuing need for therapeutic strategies that consistently stimulate protective immunity.

SUMMARY

The present invention is based, in part, on our discovery of non-naturally occurring proteins that can be used to selectively bind multiple targets, one of which is an activating Fc receptor (FcR). The proteins, which we may refer to as "engineered proteins," are non-naturally occurring in the sense that they include amino acid sequences that are not normally a part of the same protein or protein complex. Further, the amino acid sequence(s) within the engineered protein can include one or more mutations that are introduced to alter the protein's ability to bind a target. For example, the mutation may result in binding a target (e.g., an activating FcR such as FcγRIIA or FcγRIIIA) that previously would not have been bound or in increasing the binding affinity for the target.

Accordingly, the present invention features engineered proteins that include a first polypeptide that specifically binds a first target (e.g., a cellular target, such as a cell-surface antigen) and a second polypeptide that selectively binds an activating FcR. In some embodiments, the first polypeptide may specifically bind the first target by acting together with another polypeptide (i.e., the first polypeptide can be a part of a protein complex, including a tetrameric immunoglobulin of the IgG class). As described further below, the first target can be bound by an immunoglobulin, and the "first" polypeptide may therefore be a variable domain of either the immunoglobulin's light chain ($V_L$) or heavy chain ($V_H$). More specifically, the first polypeptide can be an Fab fragment of a single chain antibody (scFv).

The first and second polypeptides can be covalently bound to one another. For example, the first and second polypeptides can be joined by a peptide bond such that the resulting engineered protein is a fusion protein. As the first and second polypeptides will differ in their amino acid sequence, we may refer to them as "heterologous" polypeptides. Either polypeptide can be of a full length (i.e., it can have as many amino acid residues as its naturally-occurring counterpart) or less than full length (i.e., it can be a fragment of its naturally-occurring counterpart that retains the ability to bind a target, including, in the case of the second polypeptide, a domain of fibronectin). Additional sequence can also be included. For example, the first and second polypeptides may be joined by a peptide linker. Where the engineered protein has more than two polypeptides, they may be variously joined by additional linkers. The first and second polypeptides can also be joined by disulphide bonds or, as noted above, be included within a protein complex in which one or more polypeptides are joined (e.g., by disulphide bonds). In other embodiments, the first and second polypeptides can form the engineered protein by association within a non-covalent complex.

Amino acid sequences derived from any species, including Homo sapiens, can be used. Accordingly, the first or second polypeptide can be a human polypeptide or derived from a human polypeptide (e.g., it may be a polypeptide that differs from a naturally occurring human sequence due to the introduction of one or more mutations). Where the first or second polypeptide is within an immunoglobulin, the immunoglobulin can be a human or humanized immunoglobulin. Of course, proteins from other mammals, including rodents, can be used (particularly where veterinary applications are indicated; the polypeptides incorporated into the engineered protein can be from the same genus or species of animal being treated).

Various types of polypeptides can be used as either the first or second polypeptide, and the first and second polypeptides can be of the same type. For example, the engineered protein can be a bispecific diabody, which includes $V_H$ and $V_L$ of an immunoglobulin that binds a first target and $V_H$ and $V_L$ of an immunoglobulin that binds a second target. Thus, the first and second polypeptides can be of the same type; both can be a variable region of an immunoglobulin chain.

More generally, the first and/or the second polypeptide can be an immunoglobulin chain or an antigen-binding fragment thereof. For example, the engineered protein can include an immunoglobulin (i.e., a protein complex) or an antigen-binding fragment thereof in which the first polypeptide and/or the second polypeptide includes at least three complementarity determining regions. The immunoglobulin can be a member of the G class (i.e., an IgG).

Where the engineered protein includes an immunoglobulin that has an Fc region, the Fc region can be mutated to attenuate glycosylation. For example, the Fc region can include a mutation in or adjacent to an N-linked glycosylation site (e.g., the mutation can be at position 297; e.g., N297Q).

In other embodiments, the engineered protein can include a first polypeptide and/or a second polypeptide that is an immunoglobulin-like molecule (e.g., an AdNectin™ or iMab). The immunoglobulin-like molecule can also be a mutant fibronectin type III domain (e.g., the tenth domain; $^{10}$Fn3), with the mutation occurring in the BC loop, the DE loop, or the FG loop. As noted above, industrial Molecular affinity bodies (iMabs) can also be used (see WO 03/050283). Thus, the immunoglobulin-like molecule can include a mutant β sandwich. For example, the immunoglobulin-like molecule can include a binding peptide and a core comprising a 4-stranded β barrel, the barrel being configured such that two of the strands form a first β sheet, two of the strands form a second β sheet, and the binding peptide connects two of the strands in the β barrel.

In other embodiments, the engineered protein can include a first polypeptide and/or a second polypeptide that includes a mutant lipocalin or a target-binding fragment thereof.

In other embodiments, the engineered protein can include a first polypeptide and/or a second polypeptide within the "single loop" class of molecules that are known in the art to include microbodies, Kunitz domains, and peptide aptamers. Accordingly, the first and/or the second polypeptide can include a single peptide loop extending from a protein scaffold.

In other embodiments, the engineered protein can include a first polypeptide and/or a second polypeptide within the "secondary structure" class of molecules that are known in the art to include affibodies, DARPins, and affilins. Thus, the first polypeptide and/or the second polypeptide can include a side chain displayed on a rigid secondary structure (e.g., an α-helix bundle or a β sheet). The rigid secondary structure can be derived from a number of sources. For example, the structure can include a three-helix bundle derived from an IgG-binding domain of Protein A (e.g., the Z domain); from a designed ankyrin repeat protein (DARPin); or from γ-crystallin and ubiquitin.

Where the engineered protein is a protein complex, the first and/or second polypeptide can reside within a homo-trimeric complex that includes a C-type lectin domain and a coiled-coil trimerization module. In other embodiments, the protein complex can be an avimer and, as noted above, the engineered protein can be a diabody.

In particular embodiments, wherein the second polypeptide is an immunoglobulin-like molecule, the engineered proteins can include a first polypeptide that specifically binds a cellular target and a second polypeptide that specifically binds an activating Fc receptor, wherein the second polypeptide comprises a sequence that is at least 70% identical to a wild type Fn3 domain (e.g., SEQ ID NO:1). The sequence can include at least one mutation relative to the wild type domain, and the mutation can be a substitution, addition, or deletion mutation (e.g., a substitution or deletion of at least one amino acid residue). More specifically, the mutation can include a substitution or deletion of at least one amino acid residue in the BC loop and/or the DE loop and/or the FG loop. In any of the embodiments in which a mutant Fn3 domain serves as the second polypeptide, at least six of the eight amino acid residues in the BC loop can be either substituted with another amino acid residue or deleted. For example, eight of the amino acid residues in the BC loop can either be substituted with another amino acid residue or deleted. One to three amino acid residues (e.g., 1, 2, or 3) in the BC loop can be deleted.

Further, at least one of the four amino acid residues flanking the BC loop can be substituted or deleted. For example, at least one of the two amino acid residues flanking the BC loop on the amino-side can be substituted or deleted. For example, the serine residue at position 21 of SEQ ID NO:1 can be substituted (e.g., with an asparagine residue (N)). Alternatively, or in addition, at least one of the two amino acid residues flanking the BC loop on the carboxy-side can be substituted or deleted. For example, the tyrosine (Y) residue at position 31 of SEQ ID NO:1 can be deleted.

In any of the embodiments in which a mutant Fn3 domain serves as the second polypeptide, at least three of the five amino acid residues in the DE loop can either be substituted with another amino acid residue or deleted. For example, all five of the amino acid residues in the DE loop can be either substituted with another amino acid residue or deleted. One of the amino acid residues in the DE loop can be deleted.

In any of the embodiments in which a mutant Fn3 domain serves as the second polypeptide, at least eight of the ten amino acid residues in the FG loop can be either substituted with another amino acid residue or deleted. For example, all ten of the amino acid residues in the FG loop can be either substituted with another amino acid residue or deleted. At least three amino acid residues in this loop can be deleted.

Further, at least one of the two amino acid residues flanking the FG loop can be substituted with another amino acid residue. For example, the threonine (T) residue at position 76 of SEQ ID NO:1 can be substituted with an alanine (A) residue and/or the proline (P) residue at position 87 of SEQ ID NO:1 can be substituted with a serine (S) residue.

In particular embodiments, in the engineered proteins, at least six of the eight amino acid residues in the BC loop, at least three of the five amino acid residues in the DE loop, and at least eight of the ten amino acid residues in the FG loop are either substituted with another amino acid residue or deleted.

The engineered proteins can include a second polypeptide including the sequence CTHLHRD (SEQ ID NO: 36), AMDKAL (SEQ ID NO: 37), DLPFSDS (SEQ ID NO: 38), DMPFSDS (SEQ ID NO: 39), DLPFSDS (SEQ ID NO: 40), ALCPG (SEQ ID NO: 41), GPLSA (SEQ ID NO: 42), GPLST (SEQ ID NO: 43), GTDSI (SEQ ID NO: 44), GTESI (SEQ ID NO: 45), GTDSL (SEQ ID NO: 46), VGEDVWS (SEQ ID NO: 47), LYYDY (SEQ ID NO: 48), VGEDVWS (SEQ ID NO: 49), SSGSN (SEQ ID NO: 50), SGGFN (SEQ ID NO: 51), or SSGSS (SEQ ID NO: 52) or any combination thereof with respect to the three loops in which mutations are introduced.

The engineered proteins can include a sequence having a mutation at position 2, 5, 7, 11-12, 14, 35, 37-38, 46-50, 53-54, 56, 59, 70, 61, 63, 67, 70, 73, 90, 92-94, 96-98, or 100-101 of SEQ ID NO:1.

The engineered proteins can include a second polypeptide represented by SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, or SEQ ID NO: 35. Polypeptides exhibiting at least 85% identity (e.g., at least 85%, 90%, 95%, or 98% identity) with these sequences can also be included.

The second polypeptide can have an affinity for the activating FcR of about 100 nM and can have a higher affinity for an activating FcR than for an inhibitory FcR. The activating Fc receptor can be FcγRIIA or FcγRIIIA.

In any of the engineered proteins, the first polypeptide can be a part of a protein complex. For example, the first polypeptide can include at least three complementarity determining regions and the protein complex can be an immunoglobulin or can include an antigen-binding fragment thereof (e.g., the first polypeptide can be the light chain of an immunoglobulin). The immunoglobulin can be an immunoglobulin of the G class (IgG; e.g., an IgG1).

The cellular target can be a cancer antigen. For example, an engineered protein can include a first polypeptide that specifically binds HER-2/neu, MAGE-1, MAGE-3, BAGE, GAGE-1, GAGE-2, MUM-1, CDK4, MUC-1, N-acetylglucosaminyltransferase, p15, gp75, beta-catenin, human papillomavirus E6 protein, human papillomavirus E7protein, ErbB2, or cancer antigen 125 (CA-125).

Any of the second polypeptides (e.g., second polypeptides that specifically bind an activating Fc receptor and include a sequence that is at least 70% identical to an Fn3 domain) can be included in engineered proteins that include, as the first polypeptide/polypeptide complex, a known therapeutic antibody or an antigen binding fragment thereof. For example, the engineered protein can include one of the following immunoglobulins: abciximab (ReoPro™), adalimumab (Humira™), alemtuzumab (Campath™), basiliximab (Simulect™), bevacizumab (Avastin™), certuximab (Erbitux™), certolizumab pegol (Cimzia™), daclizumab (Zenapax™), eculizumab (Soliris™), efalizumab (Raptiva™), gemtuzumab (Mylotarg™), ibritumomab tiuxetan (Zevalin™), Infliximab (Remicade™), muromonab-CD3 (Orthoclone OKT3™), natalizumab (Tysabri™), omalizumab (Xolair™), palivizumab (Synagis™), panitumumab (Vectibix™), ranibizumab (Lucentis™), rituximab (Rituxan™, Mabthera™), tositumomab (Bexxar™), or trastuzumab (Herceptin™). In these embodiments (i.e., where the first polypeptide is, or is a part of, an immunoglobulin), the second polypeptide can be covalently bound to a terminal portion of the immunoglobulin or the antigen binding fragment thereof. Alternatively, or in addition, the second polypeptide can be inserted into the immunoglobulin or the antigen binding fragment thereof in a position that does not substantially interfere with the ability of the first polypeptide (e.g., the known therapeutic immunoglobulin) to specifically bind its antigen.

Any of the engineered proteins may be immobilized on a solid support (for example, a bead or chip), and these proteins may be arranged in any configuration on the solid support, including an array.

Also within the scope of the present invention are nucleic acid constructs that include a sequence encoding the first polypeptide and/or the second polypeptide. The constructs can include coding and non-coding sequence. For example, one or more sequences can be placed downstream from a regulatory sequence or incorporated into an expression vector (e.g., a plasmid). Any of the nucleic acid constructs can be within a host cell (e.g., a bacterial cell), and any of the nucleic acids, expression vectors, or engineered proteins can be formulated as a pharmaceutical composition. Further, more than one type of engineered protein can be included in a given pharmaceutical composition. For example, a pharmaceutical composition can include an engineered protein having a second polypeptide that selectively binds FcγRIIA and an engineered protein having a second polypeptide that selectively binds FcγRIIIA.

Host cells comprising the expression vectors described herein and pharmaceutical compositions that include any of the engineered proteins are also within the scope of the present invention.

The engineered proteins can be used to treat patients. For example, one can identify a patient diagnosed as having cancer and administer to the patient a therapeutically effective amount of an engineered protein that specifically binds a cancer antigen associated with the type of cancer affecting the patient. The first polypeptide can be a part of an immunoglobulin that specifically binds a cancer antigen undesirably expressed in the patient.

Methods of making the engineered proteins are also within the scope of the present invention. For example, where the engineered protein includes an immunoglobulin and, fused thereto (e.g., fused to the Fc region), a mutant fibronectin domain that selectively binds an activating Fc receptor, the manufacturing method can be carried out by: (a) displaying a library of randomly mutated fibronectin type III domains on the surface of a cell; (b) identifying a mutated domain having a higher binding affinity for an activating Fc receptor than for an inhibitory FcR; and (c) fusing the domain identified in step (b) with an immunoglobulin.

For example, a method of making the an engineered protein can include the steps of: (a) displaying a library of randomly mutated fibronectin type III domains on the surface of a cell; (b) identifying a mutated domain having a higher binding affinity for an activating Fc receptor than for an inhibitory FcR; (c) generating an expression construct comprising a sequence encoding the mutated domain and a sequence encoding the first polypeptide; and (d) introducing the expression construct to a cell under conditions in which the sequence encoding the mutated domain and the sequence encoding the first polypeptide are expressed as the engineered protein.

Polypeptides made by the methods described herein are also within the scope of the present invention.

The details of one or more embodiments of the invention are set forth in the accompanying drawings and the description below. Other features, objects, and advantages of the invention will be apparent from the description and drawings, and from the claims.

Figure 1:
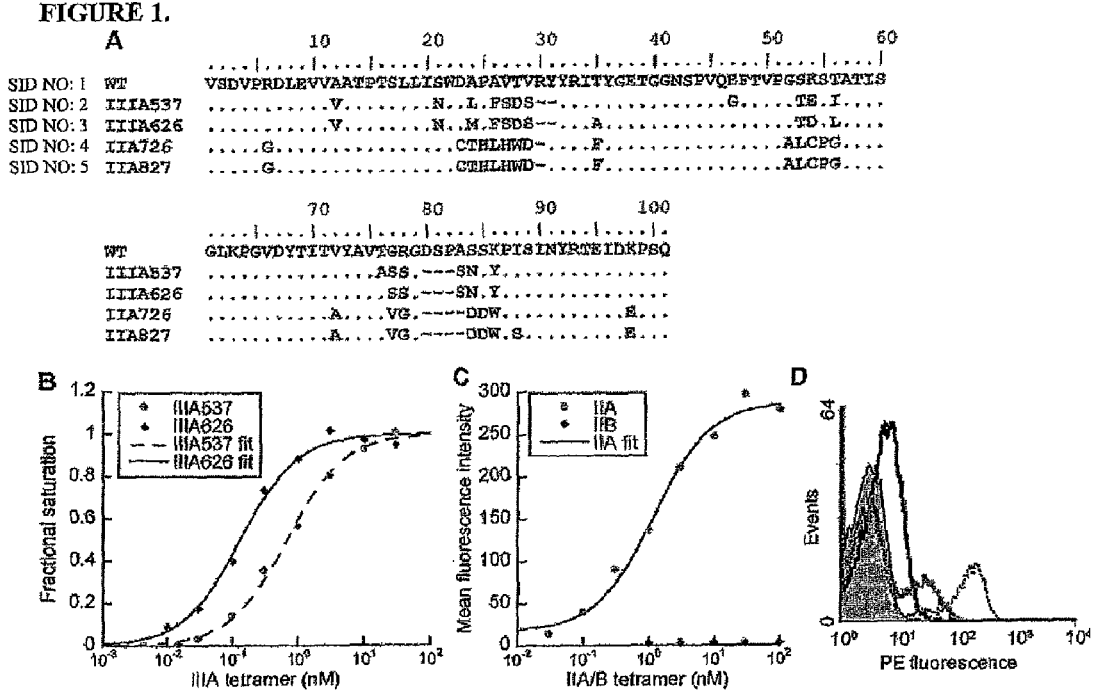
FIG. 1 depicts sequences and binding curves of selected Fn3 domains to target FcRs.

Panel (A) shows an alignment of the sequences of mutant Fn3 polypeptides with wild type Fn3. Dots indicate conserved positions, and dashes indicate deletions.

Panel (B) is a graph depicting binding curves for yeast surface-displaying clones IIIA537 and IIIA626, which were incubated with various concentrations of RIIIA$^{158F\ 176F}$ tetramer (complexed to streptavidin-PE) for 2 hours at room temperature. The yeast cells were washed and analyzed by flow cytometry. The mean PE fluorescence intensities were fitted to binding isotherms (with proportionality and background constants) to give apparent RIIIA tetramer Kd values of 0.67 nM for IIIA537 and 0.13 nM for IIIA626.

Panel (C) is a graph depicting yeast surface-displaying clone IIA726 that were incubated with various concentrations of either RIIA131R or RIIB tetramer (complexed to streptavidin-PE) for 2 hours at room temperature. The yeast cells were washed and analyzed by flow cytometry. The curve fit for the RIIA data points is to a binding isotherm (apparent Kd=1.2 nM) with proportionality and background constants.

Panel (D) is a graph depicting a flow cytometry analysis. Each Fn3 domain was produced as a C-terminal fusion to MBP and biotinylated. Pre-incubated mixtures of each biotinylated MBP-Fn3 with streptavidin-PE were used to label human PBMCs for analysis by flow cytometry. Cells were gated by forward and side scatter to exclude lymphocytes.

Gray fill histogram: MBP alone, black line: MBP-IIA726, gray line: MBP-IIIA537, dotted line: MBP-IIIA626.

FIG. 2 depicts amino acid sequences of selected mutant Fn3 domains.

DETAILED DESCRIPTION

Disclosed herein are engineered proteins that specifically bind a cellular target (e.g., a cancer antigen) and also selectively bind to an activating FcR. Preferably, there is little if any binding to the inhibitory Fc receptor (FcγRIIB). Where the cellular target is a cancer-specific antigen, the engineered proteins can be used as cancer therapeutics having improved functionality, as evidenced by an ability to recruit immune effectors. FcγR engagement is essential to the function of IgG in both immunity and in antibody-based therapies. IgGs act as the adaptor between a pathogen and the immune response by simultaneously binding antigen through their variable regions and activating an immune response through interaction of conserved Fc regions with FcγRs on cells of the immune system.

The human FcγR (hFcγR) family consists of the activating receptors hFcγRI (RI), hFcγRIIA (RIIA), and hFcγRIIIA (RIIIA), and the inhibitory receptor hFcγRIIB (RIIB). While RI binds IgG with high affinity (nanomolar binding constants), RIIA, RIIB, and RIIIA bind IgG with micromolar affinity, becoming activated only via avid multivalent interactions with opsonized antigen.

Cellular targets: The engineered proteins of the present invention are useful therapeutic proteins and can specifically bind to cellular targets (e.g., cell surface proteins and antigens) implicated in a wide range of diseases or disorders (e.g., cancer). The cancer antigen can be a tumor-associated antigen (TAA), for example a molecule (e.g., a polypeptide, carbohydrate or lipid) that is expressed by a tumor cell and either (a) differs qualitatively from its counterpart expressed in normal cells, or (b) is expressed at a higher level in tumor cells than in normal cells. Thus, a TAA can differ from (e.g., differ by one or more amino acid residues where the molecule is a protein), or it can be identical to, its counterpart expressed in normal cells. The cellular target is preferably not expressed by normal cells. Alternatively, it can be expressed at a level at least two-fold higher (e.g., at least two-fold, three-fold, five-fold, ten-fold, 20-fold, 40-fold, 100-fold, 500-fold, 1,000-fold, 5,000-fold, or 15,000-fold higher) in a diseased cell (e.g., a tumor cell) than in the cell's normal counterpart.

Examples of cancers that can be treated with the engineered proteins include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such ovarian cancer, vaginal cancer, bladder cancer, testicular cancer, prostate cancer or penile cancer, bone tumors, and vascular tumors. Examples of specific TAA's include, without limitation, HER-2/neu, MAGE-1, MAGE-3, BAGE, GAGE-1, GAGE-2, MUM-1, CDK4, MUC-1, N acetyl-glucosaminyltransferase, p15, gp75, beta-catenin, human papillomavirus E6 protein, human papillomavirus E7protein, ErbB2, or cancer antigen 125 (CA-125), carcinoembryonic antigen (CEA), RAGE, MART (melanoma antigen), MUC (mucin) (e.g., MUC-1, MUC-2, etc.), tyrosinase, Pmel 17 (gp100), GnT-V intron V sequence (N-acetylglucosaminyltransferase V intron V sequence), Prostate cancer psm, PRAME (melanoma antigen), β-catenin, EBNA (Epstein-Barr Virus nuclear antigen) 1-6, p53, lung resistance protein (LRP) Bc1-2, prostate specific antigen (PSA), and Ki-67. The "first" polypeptide as described herein can be one that specifically binds any of these molecules.

Engineered proteins: We tend to use the term "protein" to refer to longer or larger amino acid polymers, and we tend to use the term "polypeptide" to refer to shorter sequences or to a chain of amino acid residues within a larger molecule (e.g., within a fusion protein) or complex. Both terms, however, are meant to describe an entity of two or more subunit amino acids, amino acid analogs, or other peptidomimetics, regardless of post-translational modification (e.g., amidation, phosphorylation or glycosylation). The subunits can be linked by peptide bonds or other bonds such as, for example, ester or ether bonds. The terms "amino acid" and "amino acid residue" refer to natural and/or unnatural or synthetic amino acids, which may be D- or L-form optical isomers.

Immunoglobulins: The first and/or second polypeptides within the engineered proteins may be, or may be a part of, an immunoglobulin. The immunoglobulins can assume various configurations and encompass proteins consisting of one or more polypeptides substantially encoded by immunoglobulin genes. We may use the term "immunoglobulin" synonymously with "antibody."

An immunoglobulin can be a tetramer (e.g., an antibody having two heavy chains and two light chains) or a single-chain immunoglobulin, and any of the polypeptides in the tetramer or the single polypeptide of the single chain antibody may be used as the first and/or second polypeptide of the present engineered proteins. Accordingly, the first and/or second polypeptide can be one of the two heavy chains or heavy chain variable regions or one of the two light chains or light chain variable regions. The VHC and VLC regions are further subdivided into regions of hypervariability, termed "complementarity determining regions" (CDRs), interspersed with the more conserved framework regions (FRs). The extent of the FRs and CDRs has been defined (see, Kabat, E. A., et al. *Sequences of Proteins of Immunological Interest*, Fifth Edition, U.S. Department of Health and Human Services, NIH Publication No. 91-3242, 1991, and Chothia, et al., *J. Mol. Biol.* 196:901-917, 1987, which are incorporated herein by reference).

The $V_H$ or $V_L$ chain of an immunoglobulin can further include all or part of a heavy or light chain constant region. For example, the present first and second polypeptides can be within an immunoglobulin tetramer of two heavy immunoglobulin chains and two light immunoglobulin chains, wherein the heavy and light immunoglobulin chains are interconnected by, e.g., disulfide bonds. The heavy chain constant region includes three domains: CH1, CH2 and CH3. The light chain constant region is comprised of one domain: CL. The variable regions of the heavy and light chains contain a binding domain that interacts with an antigen. The polypeptides may be those of intact immunoglobulins of types IgA, IgG, IgE, IgD, IgM (as well as subtypes thereof (e.g., $IgG_1$, $IgG_2$, $IgG_3$, and $IgG_4$)), and the light chains of the immunoglobulin may be of types kappa or lambda. The recognized human immunoglobulin genes include the kappa, lambda, alpha ($IgA_1$ and $IgA_2$), gamma ($IgG_1$, $IgG_2$, $IgG_3$, $IgG_4$), delta, epsilon, and mu constant region genes, as well as the myriad immunoglobulin variable region genes.

Polypeptides within the engineered proteins of the present invention may include CDRs from a human or non-human source. The framework of the immunoglobulin can be human, humanized, or non-human (e.g., a murine framework modified to decrease antigenicity in humans), or a synthetic framework (e.g., a consensus sequence). Humanized immunoglobulins are those in which the framework residues correspond to human germline sequences and the CDRs result from V(D)J recombination and somatic mutations. However, humanized immunoglobulins may also comprise amino acid residues not encoded in human germline immunoglobulin nucleic acid sequences (e.g., mutations introduced by random or site-specific mutagenesis ex vivo). It has been demonstrated that in vivo somatic mutation of human variable genes results in mutation of framework residues (see *Nat. Immunol.* 2:537, 2001). Such an antibody would be termed "human" given its source, despite the framework mutations. Mouse antibody variable domains also contain somatic mutations in framework residues (See *Sem. Immunol.* 8:159, 1996). Consequently, transgenic mice containing the human Ig locus produce immunoglobulins that are commonly referred to as "fully human," even though they possess an average of 4.5 framework mutations (*Nature Genet.* 15:146-56, 1997). Accepted usage therefore indicates that an antibody variable domain gene based on germline sequence but possessing framework mutations introduced by, for example, an in vivo somatic mutational process is termed "human." As noted above, the present engineered proteins encompass those that specifically bind a cellular target and a activating Fc receptor even where those proteins include mutations (e.g., mutations within the FR) and fragments or other variants thereof (e.g., single chain antibodies that include the VLC and VHC of a multimeric human antibody).

The term "antigen-binding portion" of an immunoglobulin or antibody (or simply "antibody portion," or "portion"), as used herein, refers to a portion of an immunoglobulin that specifically binds to a cellular target. An antigen-binding portion of an immunoglobulin is therefore a molecule in which one or more immunoglobulin chains are not full length, but which specifically binds to a cellular target. Examples of antigen-binding portions or fragments that can be used in the present proteins include: (i) an Fab fragment, a monovalent fragment consisting of the VLC, VHC, CL and CH1 domains; (ii) a F(ab')$_2$ fragment, a bivalent fragment comprising two Fab fragments linked by a disulfide bridge at the hinge region; (iii) a Fd fragment consisting of the VHC and CH1 domains; (iv) a Fv fragment consisting of the VLC and VHC domains of a single arm of an antibody, (v) a dAb fragment (Ward et al., *Nature* 341:544-546, 1989), which consists of a VHC domain; and (vi) an isolated complementarity determining region (CDR) having sufficient framework to specifically bind, e.g., an antigen binding portion of a variable region. An antigen-binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al., *Science* 242:423-426, 1988; and Huston et al., *Proc. Natl. Acad. Sci. USA* 85:5879-5883, 1988). Such single chain antibodies are also intended to be encompassed within the term "antigen-binding portion" of an antibody.

These antibody portions are obtained using conventional techniques known to those with skill in the art, and the portions are screened for utility in the same manner as are intact antibodies. An Fab fragment can result from cleavage of a tetrameric antibody with papain; Fab' and F(ab')$_2$ fragments can be generated by cleavage with pepsin.

In summary, single chain immunoglobulins, and chimeric, humanized or CDR-grafted immunoglobulins, including those having polypeptides derived from different species, can be incorporated into the engineered proteins.

The various portions of these immunoglobulins can be joined together chemically by conventional techniques, or can be prepared as contiguous polypeptides using genetic engineering techniques. For example, nucleic acids encoding a chimeric or humanized chain can be expressed to produce a contiguous polypeptide. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman et al., *BioTechnology* 10:1455-1460, 1992, regarding CDR-graft antibody, and Ladner et al., U.S. Pat. No. 4,946,778 and Bird, R. E. et al., *Science* 242: 423-426, 1988 regarding single chain antibodies.

Nucleic acid (e.g., DNA) sequences coding for any of the polypeptides within the present engineered proteins are also within the scope of the present invention as are methods of making the engineered proteins. For example, variable regions can be constructed using PCR mutagenesis methods to alter DNA sequences encoding an immunoglobulin chain, e.g., using methods employed to generate humanized immunoglobulins (see e.g., Kanunan, et al., *Nucl. Acids Res.* 17: 5404, 1989; Sato, et al., *Cancer Research* 53: 851-856, 1993; Daugherty, et al., *Nucleic Acids Res.* 19(9): 2471-2476, 1991; and Lewis and Crowe, *Gene* 101: 297-302, 1991). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

Other suitable methods of producing or isolating immunoglobulins that specifically recognize a cellular target include, for example, methods that rely upon immunization of transgenic animals (e.g., mice) capable of producing a full repertoire of human antibodies (see e.g., Jakobovits et al., *Proc. Natl. Acad. Sci. USA* 90: 2551-2555, 1993; Jakobovits et al., *Nature* 362: 255-258, 1993; Lonberg et al., U.S. Pat. No. 5,545,806; Surani et al., U.S. Pat. No. 5,545,807). These U.S. patents are incorporated by reference herein.

The binding affinities of an immunoglobulin or of any of the other types of binding entities useful in the presently engineered proteins can be readily determined by one of ordinary skill in the art, for example, by Scatchard analysis (Scatchard, *Ann. NY Acad. Sci.* 51:660-672, 1949). For example, the immunoglobulins can bind with high affinity of $10^{-4}$ M or less, $10^{-7}$M or less, $10^{-9}$M or less or with subnanomolar affinity (0.9, 0.8, 0.7, 0.6, 0.5, 0.4, 0.3, 0.2, 0.1 nM or even less). Immunoglobulins may also be described or specified in terms of their binding affinity for their specific cellular targets. Where the target is an activating Fc receptor, the affinity of the binding polypeptide, e.g., a mutant Fn3, is preferably about 100 nM (and preferably below the micromolar range, e.g., 50 nM, 60 nM, 70 nM, 80 nM, 90 nM, 100 nM, 150 nM, 180 nM, 200 nM, 250 nM, 280 nM, 300 nM, 350 nM, 380 nM, 400 nM, 450 nM, 480 nM, 500 nM.)

The immunoglobulins may be modified to reduce or abolish glycosylation. An immunoglobulin that lacks glycosylation may be an immunoglobulin that is not glycosylated at all; that is not fully glycosylated; or that is atypically glycosylated (i.e., the glycosylation pattern for the mutant differs from the glycosylation pattern of the corresponding wild type immunoglobulin). The IgG polypeptides include one or more (e.g., 1, 2, or 3 or more) mutations that attenuate glycosylation, i.e., mutations that result in the an IgG CH2 domain that lacks glycosylation, or is not fully glycosylated or is atypically glycosylated. The mutations can be in or adjacent to an N-linked glycosylation site, for example, within the C'/E loop of the CH2 domain. Mutations at positions 297, 298 and 299 of human IgG1 are two examples of such mutations. The mutant IgGs can also include mutations in the CH2 domain outside the C'/E loop, for example, at position 290, e.g., K290N, K290E, or at position 326, e.g., K326E.

The immunoglobulin can be, for example, a known therapeutic antibody or fragment thereof. The therapeutic antibody can be an antibody that is administered to a patient in whom it is desirable to enhance an immune response. Exemplary immunoglobulins are listed below. Each immunoglobulin is identified by its proper name and its trade name. Numbers in parenthesis beginning with "DB" refer to the identifiers for each antibody on The DrugBank database available at the University of Alberta. The DrugBank database is described in Wishart D S, Knox C, Guo A C, et al. (2008). "DrugBank: a knowledgebase for drugs, drug actions and drug targets". Nucleic Acids Res. 36 (Database issue): D901-6 and can be accessed at www.drugbank.ca. Useful immunoglobulins include: Abciximab (ReoPro™) (DB00054), the Fab fragment of the chimeric human-murine monoclonal antibody 7E3, the synthesis of which is described in EP0418316 (A1) and WO8911538 (A1), which are herein incorporated by reference; Adalimumab (Humira™) (DB00051), a fully human monoclonal antibody that binds to Tumor Necrosis Factor alpha (TNF-α) and blocks TNF-α binding to its cognate receptor; alemtuzumab (Campath™) (DB00087), a humanized monoclonal antibody that targets CD52, a protein present on the surface of mature lymphocytes, used in the treatment of chronic lymphocytic leukemia (CLL), cutaneous T cell lymphoma (CTCL) and T-cell lymphoma; basiliximab (Simulect™) (DB00074), a chimeric mouse-human monoclonal antibody to the α chain (CD25) of the IL-2 receptor; bevacizumab (Avastin™) (DB00112) a humanized monoclonal antibody that recognises and blocks vascular endothelial growth factor (VEGF), the chemical signal that stimulates angiogenesis, the synthesis of which is described in Presta L G, Chen H, O'Connor S J, et al Humanization of an anti-vascular endothelial growth factor monoclonal antibody for the therapy of solid tumors and other disorders. Cancer Res, 57: 4593-9, 1997; certuximab (Erbitux™) (DB00002), a chimeric (mouse/human) monoclonal antibody that binds to and inhibits the epidermal growth factor receptor (EGFR), the synthesis of which is described in U.S. Pat. No. 6,217,866, which is herein incorporated by reference; certolizumab pegol (Cimzia™), a PEGylated Fab' fragment of a humanized TNF inhibitor monoclonal antibody; daclizumab (Zenapax™) (DB00111), a humanized monoclonal antibody to the alpha subunit of the IL-2 receptor; eculizumab (Soliris™), a humanized monoclonal antibody that binds to the human C5 complement protein; efalizumab (Raptiva™) (DB00095), a humanized monoclonal antibody that binds to CD11a; gemtuzumab (Mylotarg™) (DB00056) a monoclonal antibody to CD33 linked to a cytotoxic agent, the amino acid sequence of which is described in J Immunol 148:1149, 1991) (Caron P C, Schwartz M A, Co M S, Queen C, Finn R D, Graham M C, Divgi C R, Larson S M, Scheinberg D A. Murine and humanized constructs of monoclonal antibody M195 (anti-CD33) for the therapy of acute myelogenous leukemia. Cancer. 1994 Feb. 1; 73(3 Suppl):1049-56); ibritumomab tiuxetan (Zevalin™) (DB00078), a monoclonal mouse IgG1 antibody ibritumomab in conjunction with the chelator tiuxetan and a radioactive isotope (yttrium-90 or indium-111); Infliximab (Remicade™) (DB00065), a chimeric mouse-human monoclonal antibody that binds to tumour necrosis factor alpha (TNFα), the synthesis of which is described in U.S. Pat. No. 6,015,557, which is herein incorporated by reference; muromonab-CD3 (Orthoclone OKT3™), a mouse monoclonal IgG2a antibody that binds to the T cell receptor-CD3-complex; natalizumab (Tysabri™) (DB00108), a humanized monoclonal antibody against the cellular adhesion molecule α4-integrin, the sequence of which is described in Leger O J, Yednock T A, Tanner L, Horner H C, Hines D K, Keen S, Saldanha J, Jones S T, Fritz L C, Bendig M M. Humanization of a mouse antibody against human alpha-4 integrin: a potential therapeutic for the treatment of multiple sclerosis. Hum Antibodies. 1997; 8(1):3-16; omalizumab (Xolair™) (DB00043), a humanized IgG1k monoclonal antibody that selectively binds to human immunoglobulin E (IgE); palivizumab (Synagis™) (DB00110), a humanized monoclonal antibody (IgG) directed against an epitope in the A antigenic site of the F protein of the Respiratory Syncytial Virus (RSV), the amino acid sequence of which is described in Johnson S, Oliver C, Prince G A, Hemming V G, Pfarr D S, Wang S C, Dormitzer M, O'Grady J, Koenig S, Tamura J K, Woods R, Bansal G, Couchenour D, Tsao E, Hall W C, Young J F. Development of a humanized monoclonal antibody (MEDI-493) with potent in vitro and in vivo activity against respiratory syncytial virus. J Infect Dis. 1997 November; 176(5): 1215-24; panitumumab (Vectibix™), a fully human monoclonal antibody specific to the epidermal growth factor receptor (also known as EGF receptor, EGFR, ErbB-1 and HER1 in humans); ranibizumab (Lucentis™), an affinity matured anti-VEGF-A monoclonal antibody fragment derived from the same parent murine antibody as bevacizumab (Avastin); rituximab (Rituxan™, Mabthera™) (DB00073), a chimeric monoclonal antibody against the protein CD20, which is primarily found on the surface of B cells; tositumomab (Bexxar™) (DB00081), a anti-CD20 mouse monoclonal antibody covalently bound to $^{131}$I; or trastuzumab (Herceptin™) (DB00072) a humanized monoclonal antibody that binds selectively to the HER2 protein.

The engineered proteins can include bioequivalents of the approved or marketed antibodies (biosimilars). A biosimilar can be for example, a presently known antibody having the same primary amino acid sequence as a marketed antibody, but may be made in different cell types or by different production, purification or formulation methods. Generally any deposited materials can be used.

Immunoglobulin-like molecules: As an alternative to, or in addition to, polypeptides within immunoglobulins, the engineered proteins of the present invention can include immunoglobulin-like molecules. Immunoglobulin-like molecules include proteins that share certain structural features with immunoglobulins, for example, a β-sheet secondary structure. Examples of useful immunoglobulin-like molecules that can be engineered to selectively bind an activating Fc receptor include the following.

Fibronectin domains: The engineered proteins can include a fibronectin type III (Fn3) domain (e.g., the tenth type III domain of human Fn3). Fn3 is a small (~10 kDa), stable β-sandwich with an immunoglobulin-like fold; three exposed loops termed BC, DE, and FG are structurally analogous to antibody complementarity-determining regions (CDRs). Exemplary sequences of human fibronectin include NP_002017.1 GI:16933542; the tenth type III domain includes a region extending from about amino acids 1447 to about 1550. The positions of the BC loop, the DE loop and the FG loop are indicated in FIG. 2 by the boldfaced, underlined regions at amino acids 23-30, 52-57 and 77-86, respectively, in SEQ ID NO: 1.

The second polypeptide comprises a sequence that is at least 70% identical to a wild type Fn3 domain (e.g., SEQ ID NO:1). For example, the polypeptide can include one or more deletions, additions, and/or substitutions of, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid residues relative to a wild-type sequence. These polypeptides can also be described as exhibiting a certain degree of identity to a wild type sequence. For example, a mutant polypeptide, or the portion thereof corresponding to a wild type Fn3 domain, can be at least 50% (e.g., 51, 52, 53, 54, 55, 56, 57, 58, or 59%), at least 60% (e.g., 61, 62, 63, 64, 65, 66, 67, 68, or 69%), at least 70% (e.g., 71, 72, 73, 74, 75, 76, 77, 78, or 79%), at least 80% (e.g., 81, 82, 83, 84, 85, 86, 87, 88, or 89%), at least 90% (e.g., 91, 92, 93, 94, 95, 96, 97, 98, or 99%) identical to the corresponding wild type sequence. In some embodiments, the mutant polypeptide can be at least 50%, but less than 60%; at least 55%, but less than 65%; at least 60%, but less than 70%; at least 65%, but less than 75%; at least 65%, but less than 75%; at least 70%, but less than 80%; at least 75%, but less than 85%; at least 80%, but less than 90%; at least 85%, but less than 95% identical to the corresponding wild type sequence.

We use the terms "identity" and "identical" in connection with protein or DNA sequences to refer to the subunit sequence identity between two molecules. When a subunit position in both of the molecules is occupied by the same monomeric subunit (i.e., the same amino acid residue or nucleotide), then the molecules are identical at that position. Percent sequence identity is calculated by determining the number of matched positions in aligned amino acid sequences, dividing the number of matched positions by the total number of aligned amino acids, and multiplying by 100. A matched position refers to a position in which identical amino acids occur at the same position in aligned amino acid sequences. Percent sequence identity also can be determined for any nucleic acid sequence.

Percent sequence identity can be determined by comparing a target nucleic acid or amino acid sequence to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained on the World Wide Web from Fish & Richardson's web site (fr.com/blast) or the U.S. government's National Center for Biotechnology Information web site (ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\Bl2seq -i c:\seq1.txt -j c:\seq2.txt -p blastn -o c:\output.txt -q −1 -r 2. If the target sequence shares homology with any portion of the identified sequence, the designated output file will present those regions of homology as aligned sequences. If the target sequence does not share homology with any portion of the identified sequence, the designated output file will not present aligned sequences.

Once aligned, a length is determined by counting the number of consecutive residues from the target sequence presented in alignment with sequence from the identified sequence starting with any matched position and ending with any other matched position. A matched position is any position where an identical residue is presented in both the target and identified sequence. Gaps presented in the target sequence are not counted since gaps are not amino acids or nucleotides. Likewise, gaps presented in the identified sequence are not counted since target sequence residues are counted, not residues from the identified sequence. The percent identity over a particular length is determined by counting the number of matched positions over that length and dividing that number by the length followed by multiplying the resulting value by 100.

It will be appreciated that different regions within a single amino acid or nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Where a mutant polypeptide differs from a reference sequence (e.g., a portion of a wild type Fn3), the differences may constitute a substitution of one or more amino acid residues. The substitution can be, but is not necessarily, a "conservative" substitution. Examples of conservative substitutions include substitutions within the following groups glycine, alanine; valine, isoleucine, leucine; aspartic acid, glutamic acid; asparagine, glutamine; serine, threonine; lysine, arginine; and phenylalanine, tyrosine.

Amino acid substitutions can be made, in some cases, by selecting substitutions that do not differ significantly in their effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of useful substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine.

In some embodiments, a mutant Fn3 polypeptide can include one or more non-conservative substitutions. Non-conservative substitutions typically entail exchanging a member of one of the classes described above for a member of another class. The substitutions may also be of an amino acid residue that does not occur in nature (e.g., a beta-amino acid (e.g., β alanine or norleucine). Polypeptides can also differ from a corresponding wild type sequence by virtue of the manner in which they are post-translationally modified (e.g., glycosylated).

More specifically, the engineered proteins can include a mutant shown in FIG. 1 or FIG. 2 and having the sequence designated IIIA537 (SEQ ID NO: 2), IIIA626 (SEQ ID NO: 3), IIA726 (SEQ ID NO: 4), IIA827 (SEQ ID NO: 5), SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, or SEQ ID NO: 35.

The engineered proteins can include a second polypeptide including the sequence CTHLHRD (SEQ ID NO: 36), AMDKAL (SEQ ID NO: 37), DLPFSDS (SEQ ID NO: 38), DMPFSDS (SEQ ID NO: 39), DLPFSDS (SEQ ID NO: 40), ALCPG (SEQ ID NO: 41), GPLSA (SEQ ID NO: 42), GPLST (SEQ ID NO: 43), GTDSI (SEQ ID NO: 44), GTESI (SEQ ID NO: 45), GTDSL (SEQ ID NO: 46), VGEDVWS (SEQ ID NO: 47), LYYDY (SEQ ID NO: 48), VGEDVWS (SEQ ID NO: 49), SSGSN (SEQ ID NO: 50), SGGFN (SEQ ID NO: 51), or SSGSS (SEQ ID NO: 52) or any combination thereof with respect to the three loops in which mutations are introduced.

The engineered proteins can include a sequence having a mutation at position 2, 5, 7, 11-12, 14, 35, 37-38, 46-50, 53-54, 56, 59, 70, 61, 63, 67, 70, 73, 90, 92-94, 96-98, or 100-101 of SEQ ID NO:1.

The gaps in the sequences in FIGS. 1 and 2 are shown to illustrate the positions where deletions can be introduced into the wild type sequence but, of course, in reality the amino acid residues are contiguous and connected. Each SEQ ID NO refers to the contiguous sequence. Other useful polypeptides include mutants of the wild type fibronectin domain having mutations other than those shown but at the position shown. For example, a mutation of the wild type arginine at position 6; and/or a mutation of the wild type alanine at position 12; and/or a mutation of the wild type serine at position 21; and so forth.

Fn3 polypeptides, Fn3 polypeptide monobodies, and methods of making these compositions are described in U.S. Pat. No. 5,153,661, which is hereby incorporated by reference in its entirety. The polypeptides of U.S. Pat. No. 5,153,661 can be used in the present engineered proteins or modified to alter their binding specificity and used in the present engineered proteins. Proteins that generally make use of a scaffold derived from Fn3 are also disclosed in U.S. Pat. No. 7,115,396, which is incorporated herein by reference, and may be used to make the first and/or second polypeptides within the present engineered polypeptides.

Other constructs relying on the fibronectin type III domain include, for example, iMabs or "monobodies" described, for example, in Koide and Koide (Methods in Molecular Biology, vol 352: Protein Engineering Protocols, (2007) p. 95-109) and Adnectins or Trinectins, which are selected to include two, three or four loops that connect the strands on one end of the beta-sandwich, similar to the CDRs of an antibody.

Other members of this class include: human cytotoxic T-lymphocyte associated protein 4 (CTLA-4) which comprises CDR-like loops similar to antibodies that are permissive to loop replacements; neocarzinostatin, an enediyne-binding chromoprotein isolated from *Streptomyces carzinostaticus* which consists of seven β-strands in two sheets forming a β-sandwich, a topology similar to the immunoglobulin fold; Carbohydrate binding module 4-2, derived from the *Rhodothermus marinus* xylanase Xyn10A, which has a β-sandwich structure formed by 11 strands and contains no disulfide bonds; tendamistat, a 74-residue inhibitor of α-amylase from *Streptomyces tendae*, which includes an α-amylase-binding loop 1 permissive to randomization; and the β-barrel green fluorescent protein (GFP).

Nonimmunoglobulin scaffolds: Nonimmunoglobulin scaffolds can also be used in the engineered proteins of the invention. Examples of useful scaffolds that can be engineered to selectively bind a cellular target or an activating Fc receptor include the following general classes of polypeptides.

Scaffolds exhibiting a contiguous hypervariable loop region: Lipocalins are 160- to 180-residue polypeptides involved in storage or transport of hydrophobic and/or chemically sensitive organic compounds. They consist of a central β-barrel of eight anti-parallel β-strands, which support a set of four hypervariable loops that form the ligand binding site. The four hypervariable loops connect the β-strands in a pairwise fashion at the open end of this central folding motif. The position of the mutant amino acids depends upon the nature of the target. Typically, where a lipocalin is employed, it may include one or more mutations in the cavity, the loops, or both. Exemplary members of the lipocalin family include apolipoprotein D (ApoD) and bovine heart fatty acid-binding protein (FABP).

Single peptide loops displayed on a carrier protein: Kunitz-type inhibitors of serine proteases are a group of small, irregular protease inhibitors with few secondary structures exposing a more or less extended peptide stretch with varying sequence. Exemplary Kunitz type inhibitors of serine proteases include beef pancreas trypsin inhibitor, human lipoprotein associated coagulation inhibitor D1, human inter-α trypsin inhibitor, human pancreatic secretory trypsin inhibitor (PSTI), Alzheimer's amyloid β-protein precursor inhibitor (APPI), the leech-derived trypsin inhibitor (LTDI), the mustard trypsin inhibitor II (MTI II) and the periplasmic *E. coli* protease inhibitor ecotin.

Thioredoixins are small, highly soluble and structurally robost enzymes involved in the cytosolic thiol/disulfide equilibrium of *E. coli*. The short active site sequence of Cys-Gly-Pro-Cys forms a tight disulfide bridged and solvent accessible loop in the oxidized state and permits the insertion of long peptide stretches. Peptide aptamers have been selected from corresponding random loop libraries.

The "knottin family" comprises small, 25- to 35-residue proteins, some of which also function as protease inhibitors. They include conserved disulfide bonds, leading to a characteristic knotted topology, and interspersed variable peptide loops. They typically contain a small triple stranded antiparallel b-sheet and cysteine-knot motif that arises from three interlocking disulfide bridges. Knottin scaffolds are also known as miniproteins or microbodies. Examples of useful knottins include the trypsin inhibitor from the squirting cucumber *Ecballium elaterium* (EETI-II), the C-terminal cellulose-binding domain (CBD) of cellobiohydrolase I from the fungus *Trichoderma reesei.*

Other examples of useful scaffold proteins in this class include insect defensin A, which forms an α-helix and two β-strands, has two loop regions with tolerance for substitutions, and is stabilized by two disulfide bridges; the PDZ domain, a protein-recognition module involved in signaling networks, which contains three α-helices and five β-strands; scorpion toxins, for example, charybdotoxin from *Leiurus quinquestriatus hebraeus*, which includes a 37-residue motif consisting of an anti-parallel triple-stranded β-sheet, a short α-helix, and three stabilizing disulfide bonds; the plant homeodomain (PHD) finger protein a small protein with a well-structured core that contains two zinc ions, no disulfide bonds and two variable and flexible loops that seem to be tolerant to mutagenesis, expansion, and loop grafting; and TEM-1 β-lactamase a larger protein (263 residues) that has a protein backbone consisting of numerous α-helices and β-sheets, and a disulfide bond.

Interfaces resting on secondary structures; α-helical frameworks and β-sheets: The Z domain, one of the five stable three-α-helix bundle domains from the immunoglobulin Fc-binding region of staphylococcal protein A, is highly soluble, proteolytically and thermally stable, and does not contain disulfide bonds. Thirteen surface residues involved in Fc-binding have been randomized to generate so-called affibodies; the affinity and avidity of affibodies has been further increased by α-helix shuffling and multimerization.

Ankyrin repeat domains consist of repetitive structural units of 33 residues comprising a β-turn followed by two anti-parallel α-helices and a loop linking up to the turn of the next repeat. Designed ankyrin repeat proteins (DARPins) with up to four repeats between N- and C-terminal capping repeats can be used to generate a polypeptide that selectively binds an activating FcR. Mutations can be introduced into a number of regions, for example, the β-turn, α-helix, and loop region, representing the binding surface under natural conditions.

Other proteins that fall within this class include the consensus repeat sequence from leucine-rich repeat proteins (mammalian ribonuclease inhibitor family), and the Affilins, engineered proteins comprising two different protein scaffolds: human γ-crystallin, a durable protein from the eye lens, and human ubiquitin, a small protein normally involved in intracellular protein degradation. Also included in this class are the immunity proteins, exemplified by the all-α-coil scaffold of *E. coli* colicin E7 immunity protein (ImmE7), an 87-residue protein that contains no cysteines and folds into a four-helix bundle topology (α-helices I-IV). α-Helices I and III are followed by two loops; Cytochrome b562 a four-helix bundle protein with two loops connecting the α-helical framework; peptide α2p8, a 38-amino acid peptide, comprising an α-helical hairpin that is derived from the two N-terminal helices of the human p8MTCP1 protein (a small 8-kDa protein encoded by the human oncogene MTCP1).

Oligomeric domain structures: This class of proteins includes engineered multidomain proteins that form complexes of oligomeric structure and multiple interactions. One example of this class are the avimers, also known as maxibodies, artificial multidomain proteins derived from the human A-domains as they occur in the low-density lipoprotein receptor (LDLR). The scaffold comprises 35 amino acids, two-thirds of which may be variable, and the confirmation is determined by three disulfide bonds and a complexed calcium ion. Another example in this class is the Trinectins, homotrimeric proteins that include a C-type lectin domain (CTLD) and coiled coil trimerization module. The CTLDs share a conserved structural core, which supports a loop that forms the sugar binding site.

Methods of treatment: The engineered proteins disclosed herein are generally useful for generating immune responses and as prophylactic vaccines or immune response-stimulating therapeutics. A patient is effectively treated whenever a clinically beneficial result ensues. This may mean a complete resolution of the symptoms of a disease, a decrease in the severity of the symptoms of the disease, or a slowing of the disease's progression.

The methods disclosed herein can be applied to a wide range of species, e.g., humans, non-human primates (e.g., monkeys), horses or other livestock, dogs, cats or other mammals kept as pets, rats, mice, or other laboratory animals. The engineered proteins described herein are useful in therapeutic compositions and regimens or for the manufacture of a medicament or for the manufacture of a medicament for use in treatment of diseases or conditions as described herein (e.g., cancer).

Administration and formulation: The engineered proteins described herein can be administered directly to a mammal. Generally, the engineered proteins can be suspended in a pharmaceutically acceptable carrier (e.g., physiological saline or a buffered saline solution) to facilitate their delivery. Encapsulation of the polypeptides in a suitable delivery vehicle (e.g., polymeric microparticles or implantable devices) may increase the efficiency of delivery. A composition can be made by combining any of the peptides provided herein with a pharmaceutically acceptable carrier. Such carriers can include, without limitation, sterile aqueous or non-aqueous solutions, suspensions, and emulsions. Examples of non-aqueous solvents include mineral oil, propylene glycol, polyethylene glycol, vegetable oils, and injectable organic esters. Aqueous carriers include, without limitation, water, alcohol, saline, and buffered solutions. Preservatives, flavorings, and other additives such as, for example, antimicrobials, anti-oxidants (e.g., propyl gallate), chelating agents, inert gases, and the like may also be present. It will be appreciated that any material described herein that is to be administered to a mammal can contain one or more pharmaceutically acceptable carriers.

Any composition described herein can be administered to any part of the host's body for subsequent delivery to a target cell. A composition can be delivered to, without limitation, the brain, the cerebrospinal fluid, joints, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

The dosage required will depend on the route of administration, the nature of the formulation, the nature of the patient's illness, the patient's size, weight, surface area, age, and sex, other drugs being administered, and the judgment of the attending clinician. Suitable dosages are in the range of 0.01-1,000 μg/kg. Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the engineered proteins in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, an engineered protein can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present engineered proteins can be administered once (or twice, three times, etc.) daily, weekly, monthly, or yearly.

An effective amount of any composition provided herein can be administered to an individual in need of treatment. The term "effective" as used herein refers to any amount that induces a desired response while not inducing significant toxicity in the patient. Such an amount can be determined by assessing a patient's response after administration of a known amount of a particular composition. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

Any method known to those in the art can be used to determine if a particular response is induced. Clinical methods that can assess the degree of a particular disease state can be used to determine if a response is induced. The particular methods used to evaluate a response will depend upon the nature of the patient's disorder, the patient's age, and sex, other drugs being administered, and the judgment of the attending clinician.

Alternatively, a polynucleotide containing a nucleic acid sequence encoding an engineered protein can be delivered to an appropriate cell of the animal. This can be achieved by, for example, the use of a polymeric, biodegradable microparticle or microcapsule delivery vehicle, sized to optimize phagocytosis by phagocytic cells such as macrophages. For example, PLGA (poly-lactide-co-glycolide) microparticles approximately 1-10 µm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 µm and preferably larger than 20 µm).

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells. Delivery of "naked DNA" (i.e., without a delivery vehicle) to an intramuscular, intradermal, or subcutaneous site, is another means to achieve in vivo expression.

In the relevant polynucleotides (e.g., expression vectors) the nucleic acid sequence encoding the engineered protein with an initiator methionine and optionally a targeting sequence is operatively linked to a promoter or enhancer-promoter combination. Promoters and enhancers are described above, and many are well known in the art.

Polynucleotides can be administered in a pharmaceutically acceptable carrier. Pharmaceutically acceptable carriers are biologically compatible vehicles which are suitable for administration to a human or other mammalian subject (e.g., physiological saline). A therapeutically effective amount is an amount of the polynucleotide which is capable of producing a medically desirable result (e.g., a decrease in clinical motor symptoms) in a treated mammal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

Combination Therapy: The engineered proteins of the invention can also be administered with another therapeutic agent, such as a cytotoxic agent, or cancer chemotherapeutic. Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

In some embodiments the methods provided contemplate the administration of combinations, or "cocktails," of different engineered proteins. Such cocktails may have certain advantages inasmuch as they contain polypeptides that exploit different effector functions. Such proteins in combination may exhibit synergistic therapeutic effects. Useful engineered proteins include those that target the EGF receptor (e.g., Cetuximab (Erbitux™)), those that target VEGF (e.g., Bevacizumab (Avastin™)) and those that target Her-2 (e.g., trastuzimab (Herceptin™)).

A cytotoxic agent refers to a substance that inhibits or prevents the function of cells and/or causes destruction of cells. The term is intended to include radioactive isotopes e.g., $^{131}I$, $^{125}I$, $^{90}Y$ and $^{186}Re$), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are hereby incorporated by reference herein). Such agents may be conjugated, coupled, linked or associated with an antibody disclosed herein.

In some embodiments, conventional cancer medicaments are administered with the compositions disclosed herein. Suitable agents include those agents that promote DNA-damage, e.g., double stranded breaks in cellular DNA, in cancer cells. Any form of DNA-damaging agent know to those of skill in the art can be used. DNA damage can typically be produced by radiation therapy and/or chemotherapy. Examples of radiation therapy include, without limitation, external radiation therapy and internal radiation therapy (also called brachytherapy). Energy sources for external radiation therapy include x-rays, gamma rays and particle beams; energy sources used in internal radiation include radioactive iodine (iodine$^{125}$ or iodine$^{131}$), and from strontium$^{89}$, or radioisotopes of phosphorous, palladium, cesium, iridium, phosphate, or cobalt. Methods of administering radiation therapy are well know to those of skill in the art.

EXAMPLES

Example 1

Materials and Methods

Naïve Yeast Libraries and Culture Conditions. Three yeast surface display libraries of Fn3 were combined for screening.

The G2 library had BC, DE, and FG loops randomized in both length and composition; in the G4 library, the amino acid composition of the loops was also biased towards that in antibody CDRs. In the YS library, the BC and FG loops consisted solely of Tyr and Ser residues. In general, yeast libraries and individual clones were cultured in SD-CAA (2% dextrose, 0.67% yeast nitrogen base, 0.5% casamino acids, 0.07 M sodium citrate, pH 4.5) at 30° C., 250 rpm to an OD600 of 2-7 and induced in SG-CAA (SD-CAA with galactose replacing dextrose) at an initial OD600 of ~1 for 12-16 h at 30° C., 250 rpm.

Library Screening using Magnetic Beads. Soluble, singly biotinylated human FcRs were provided by the Ravetch group, The Rockefeller University, NY. Stoichiometric amounts of each FcR were incubated individually with $4\times10^6$ Biotin Binder Dynabeads (Invitrogen, Carlsbad, Calif., ~$6\times10^6$ biotin binding site per bead) overnight at 4° C., then washed twice using the Dynal MPC magnet. Every library sort against an FcR was preceded by two negative sorts to deplete streptavidin and biotin binders. Briefly, yeast cells were incubated for 45 minutes at 4° C. with $8\times10^6$ untreated beads or beads partially coated with biotin and/or biotin-PEG (Laysan Bio, Arab, Ala.) in 2 ml PBS+0.1% bovine serum albumin (PBSA), after which the tube was placed in the magnet for 5 minutes and the free yeast collected. For positive selection, the depleted library was incubated for 3 hours at 4° C. with the FcR-coated beads before magnetic separation. The bead-bound yeast were washed, with the number of wash steps (1-3), duration (1-15 minutes) and temperature (4° C. or 20° C.) varying as the sorts progressed to maintain the number of retrieved yeast cells at around $105-5\times10^6$. The retrieved yeast cells (with beads) were cultured in 50 ml SD-CAA and the beads were removed using the magnet prior to induction.

In the initial sorts, $8\times10^9$ yeast cells from the naïve Fn3 libraries were screened against RIIA in a single tube, after which the unbound yeast were screened against RIIIA. For subsequent sorts, enough cells were screened such that the number of expressing cells was approximately ten-fold larger than the maximum library diversity. In addition to varying the washing procedure, the stringency of the selections was also increased by reducing the avidity. From the sixth sort onwards, the number of moles of biotinylated FcR was reduced to ~20% of the number of biotin-binding sites on the beads (although the number of beads used was doubled), which was further reduced to 5% for the final sort against RIIIA. The remaining binding sites were occupied by excess biotin-PEG to reduce streptavidin exposure. Also from the sixth sort onwards, the induction time was reduced to 2.5 hours to reduce the number of Fn3 domains expressed per yeast cell. After a total of eight sorts interspersed with four rounds of mutagenesis as described below, the resulting yeast libraries exhibited clear labeling by the respective FcR (in tetrameric form bound to streptavidin) and magnetic bead sorts were abandoned in favor of fluorescence activated cell sorting (FACS).

Fn3 Mutagenesis and Electroporation. After every two sorts (or three in the caseof RIIA FACS sorts), the plasmid DNA was rescued from the yeast libraries and subjected to error-prone PCR. Briefly, a 50 µl 15-cycle error-prone PCR reaction was performed to amplify the entire Fn3 gene using 0.5 µM of each primer (see Table 1, which lists, in, order, SEQ ID Nos: 53-60), 0.2 mM of each dNTP, 2 mM each of 8-oxo-dGTP and dPTP (TriLink, San Diego, MA), Taq enzyme and Thermopol buffer (New England Biolabs, Ipswich, MA) and plasmid DNA recovered from $2\times10^7$ yeast cells (Zymoprep II kit, Zymo Research, Orange, CA). At the same time, three other PCR reactions were performed to mutagenize the BC, DE, and FG loops individually using the appropriate primers (Table D.1) and 20 mM each of 8-oxo-dGTP and dPTP. The error-prone PCR products were extracted from agarose gel and amplified by conventional PCR reactions (400 µl per product) using shortened (23-27 bp) versions of the above primers. The three loop products were precipitated using PelletPaint (Novagen, Madison, Wis.), dissolved together in 3 µl of water, and mixed with 2 µg of plasmid vector digested to remove the BG loop through the FG loop (NcoI/SmaI/NdeI-cut pCT-Fn3-Loop). The gene product was likewise concentrated to 1 µl in water and mixed with 2 µg of plasmid vector digested to remove the entire Fn3 gene as well as the $(G4S)_3$ linker (PstI/NdeI/BamHI-cut pCT-Fn3-Gene). From the fourth round of mutagenesis onwards, the mutagenized loops were also mixed with 1-2% of loops derived from the naive libraries to increase loop diversity. Each DNA mix was electroporated into 100 µl electrocompetent EBY100 yeast (from 25 ml of culture) divided between two cuvettes.

TABLE 1

Mutagenesis primers and shortened amplification primers (underlined)

| Name | Sequence | Target |
|---|---|---|
| W5 | CGACGATTGAAGGTAGATACCCATACGACGTTCCAGACTACGCTCTGCAG | Fn3 gene |
| W3 | ATCTCGAGCTATTACAAGTCCTCTTCAGAAATAAGCTTTTGTTCGGATCC | |
| BC5new | GGGACCTGGAAGTTGTTGCTGCGACCCCCACCAGCCTACTGATCAGCTGG | BC loop |
| Lbc3 | TGAACTCCTGGACAGGGCTATTTCCTCCTGTTTCTCCGTAAGTGATCCTGTAATA | |
| Lde5 | CAGGATCACTTACGGAGAAACAGGAGGAAATAGCCCTGTCCAGGAGTTCACTGTG | DE loop |
| Lde3 | GCATACACAGTGATGGTATAATCAACTCCAGGTTTAAGGCCGCTGATGGTAGC | |
| Lfg5 | ACCATCAGCGGCCTTAAACCTGGAGTTGATTATACCATCACTGTGTATGCTGTC | FG loop |
| FG3new | GATCCCTGGGATGGTTTGTCAATTTCTGTTCGGTAATTAATGGAAATTGG | |

Library Screening by FACS. For flow cytometry, biotinylated FcRs were incubated with streptavidin-PE (premium grade, Invitrogen) or streptavidin-Alexa Fluor 647 at a 4:1 molar ratio for at least 30 minutes at room temperature before use. After the eighth magnetic bead sort, the library evolved to bind to RIIIA did not display any binding to RIIB tetramer, thus further selections by FACS were focused only on improving affinity to RIIIA. Yeast libraries were incubated with PE-tagged RIIIA tetramer (at decreasing concentrations with successive sorts) in a volume of PBSA ensuring at least 3-fold excess of RIIIA over Fn3 domains for 1 h at RT. The yeast was then centrifuged and all the supernatant except for 0.1-0.5 ml was removed. Chicken α-c-myc-Alexa Fluor 647

(made by using the Microscale Protein Labeling Kit on the unconjugated IgY, both from Invitrogen) was then added prior to incubation on ice for 30 min. The yeast cells were sorted on a BD FACSAria, selecting 0.1-0.5% of the cells with the highest PE to Alexa Fluor 647 fluorescence ratio, which were collected and grown up in 5 ml SD-CAA.

For the library evolved to bind to RIIA, some binding to RIIB tetramer was also seen after magnetic sorting. Therefore, FACS selections for decreased affinity to RIIB were carried out in alternation with selections for increased affinity to RIIA (performed analogously to the RIIIA affinity sorts). For these selectivity sorts, yeast cells were incubated with Alexa Fluor 647-tagged RIIA tetramer and a higher concentration of PE-tagged RIIB tetramer for 1 h at RT prior to FACS. The cells exhibiting high RIIA binding with little or no RIIB binding were selected.

Characterization of Individual Clones. Plasmid DNA was recovered from the later library generations (Zymoprep II kit) and transformed into competent DH5a bacteria (Invitrogen). Individual colonies (usually ten) were grown, miniprepped, and sequenced, as well as re-transformed into EBY100 yeast (EZ Yeast Transformation Kit, Zymo Research). The resulting clones were cultured in SD-CAA and induced in SG-CAA for analysis. To rapidly compare different clones, 0.1 OD.ml aliquots of yeast were labeled with a low and a high concentration of PE-tagged RIIA (1 nM, 30 nM) or RIIIA (0.3 nM, 10 nM) tetramer for 1 hour at RT prior to flow cytometry (Coulter Epics XL). The apparent tetramer Kd was estimated from the ratio of the two mean fluorescence readings. To measure the apparent tetramer Kd more accurately for selected clones, yeast cells were washed and incubated with 7-8 different concentrations of PE-tagged tetramer spanning 3-4 orders of magnitude for 2 hours at RT. The labeling volumes (in PBSA) were chosen to give at least a 10-fold excess of FcR over Fn3. The yeast cells were centrifuged and washed with 0.5 ml PBSA for analysis by flow cytometry. The Kd value was determined by fitting the data to the equation y=A[tetramer]/([tetramer]+Kd)+B.

Expression and Purification of MBP-Fn3 Fusion Proteins. Selected Fn3 domains were subcloned into the pMal-c2x vector (New England Biolabs) for expression in $E.$ $coli$ as a C-terminal fusion to maltose-binding protein (MBP). A forward primer adding a flanking AvaI restriction site followed by the TEV protease site LGENLYFQS and a reverse primer adding a Stop codon and a XbaI site were used to amplify each Fn3 gene sequence. The AvaI/XbaI-digested PCR product was ligated to the similarly digested pMal-c2x backbone. After sequence confirmation, the resulting plasmid was transformed into either Rosetta(DE3) or Rosetta-gami 2(DE3) (Stratagene, La Jolla, Calif.) for expression. Freshly transformed colonies were cultured to saturation in 5 ml antibiotic-supplemented LB+glucose (10 g tryptone, 5 g yeast extract, 5 g NaCl, 2 g glucose in 1 L water) at 37° C., 250 rpm. These starter cultures were used to inoculate 100 ml (Rosetta) or 200 ml (Rosetta-gami) of antibiotic-free LB+glucose at a 1:100 ratio, which were then induced with 0.3 mM IPTG when the OD600 reached 0.6. The bacteria were pelleted by centrifugation and frozen after 1 hour induction at 37° C. The thawed pellets were resuspended in 5 ml cold column buffer (20 mM Tris-HCl, pH 7.4, 200 mM NaCl, 1 mM EDTA) with Complete Protease Inhibitor Cocktail (Roche Applied Science, Indianapolis, Ind.) and lysed by sonication. After centrifuging at 20,000×g, 15 minutes, 4° C., the supernatant was loaded onto 2 ml amylose resin (New England Biolabs) pre-equilibrated with column buffer, washed with 50 ml column buffer, and eluted with column buffer containing 10 mM maltose. The eluate was concentrated and buffer-exchanged into PBS using an Amicon Ultra-15 device (Millipore, Billerica, Mass.).

Surface Plasmon Resonance Analysis. Steady state affinity measurements were performed on a Biacore T100 biosensor. MBP-Fn3 fusion proteins were immobilized to CM5 sensor chips (Biacore) by standard amine coupling. Soluble RIIA, RIIB or RIIIA were injected in 5 different concentrations through flow cells at room temperature in HBS-EP running buffer (Biacore) for 3 minutes at a flow rate of 30 µl/min and dissociation was observed for 10 minutes. Dissociation constants were calculated after subtraction of background binding to a control flow cell using Biacore T100 Evaluation software.

Example 2

Selection and Affinity/Selectivity Maturation of Fn3 Binders to FcRs

To select for Fn3 domains that bind weakly to RIIA and RIIIA from naïve yeast surface display libraries, we performed magnetic bead sorting using streptavidin-coated beads loaded with biotinylated FcR, capitalizing on the highly multivalent interactions between yeast cells and beads. The sorting was performed according to the method in Example 1. The libraries were mutagenized by error-prone PCR according to the method in Example 1 (the entire Fn3 gene as well as focused mutagenesis of the BC, DE, and FG loops) on average after every two sorts. As the selections progressed, in addition to increasing the wash stringency, the avidity was reduced by decreasing the surface density of both Fn3 and FcR. Unless otherwise stated, the 131R allele of RIIA and the 158F 176F allele of RIIIA were used. After eight magnetic sorts and four rounds of mutagenesis, both libraries were highly enriched for yeast cells that were clearly labeled by 25 nM of their respective FcR target in tetrameric form (complexed with streptavidin-PE). The RIIIA-binding library showed no binding to RIIB tetramer at 100 nM (not shown); therefore, continued affinity maturation by FACS was performed by standard methods. To avoid unwanted side reactions between FcR and any mammalian IgG, a fluorescently tagged chicken IgY was used for expression labeling. The RIIA-targeted library displayed some binding to RIIB tetramer, albeit at a reduced level compared to RIIA tetramer, which was unsurprising given the high level of homology between the two receptors. Alternating sorts for affinity maturation and selectivity were performed. For the selectivity sorts, libraries were co-labeled with a high concentration of PE-tagged RIIB tetramer and a low concentration of Alexa Fluor 647-tagged RIIA tetramer to enrich clones that discriminated between the two receptors.

Example 3

Analysis of Selected Clones

Our goal was to engineer Fn3 domains with roughly the same affinity for RIIA and RIIB as native IgGs ($K_d$~$10^{-5}$-$10^{-6}$ M), such that the eventual IgG-Fn3 fusions would activate immune cells after antigen opsonization but not in soluble form. After four FACS sorts (with one round of mutagenesis), the RIIIA-binding library was clearly labeled by 1 µM of monovalent RIIIA and the $K_d$ was estimated to be in the range of 0.5-5 µM. Individual clones from this and previous libraries were sequenced and their relative affinities were estimated by determining the ratio of mean fluorescence intensities when labeled with a low versus high concentration of FcR tetramer. The tightest binder was IIIA626 (sequence shown in FIG. 1, panel A), which was then further characterized by titration to yield an apparent $K_d$ of 0.13 nM for RIIIA tetramer (FIG. 1, panel B). Another clone with roughly five-fold lower tetramer affinity was also selected for further characterization in case the monovalent $K_d$ of IIIA626 turned out to be too low. The apparent $K_d$ of IIIA537 for RIIIA tetramer was found to be 0.67 nM (FIG. 1, panel B).

For the RIIA-binding library, no improvement in apparent $K_d$ was seen during the eighth FACS sort (an affinity sort). Of the individual clones that were analyzed, IIA726 from the seventh FACS sort had the highest affinity for RIIA tetramer. From the titration curve, the apparent $K_d$ for RIIA tetramer was 1.2 nM, whereas binding to RIIB tetramer was undetectable even at 100 nM (FIG. 1, panel C). A new library was subsequently created by mutagenizing IIA726. After two sorts, clone IIA827 with a single mutation (I88S) was identified as having improved affinity for RIIA tetramer (0.54 nM apparent $K_d$) while retaining undetectable binding for 100 nM RIIB tetramer. Unlike the cysteine-free RIIIA binders, IIA726 and IIA827 contain a pair of Cys residues in the BC and DE loops (FIG. 1, panel A).

Example 4

Soluble MBP-Fn3 Fusion Proteins

The selected Fn3 domains were each produced as C-terminal fusions to MBP for determining the affinities for FcRs using surface plasmon resonance (SPR). Fusion proteins were generated and purified according to Example 1. MBP was chosen as a fusion partner because it contains many lysine residues available for amine coupling and acts as a chaperone, increasing the yields of soluble protein expressed in *E. coli*. MBP fusions of IIIA537, IIIA626 and IIA726 were initially expressed in the strain Rosetta(DE3) at high yields (3-5 mg from 100 ml of culture) and purified by amylose affinity chromatography. MBP-IIIA537 and MBP-IIIA626 were able to block the binding of PE-tagged RIIIA tetramer to yeast surface-displaying IIIA537. The ability of MBP-IIA726 to block RIIA tetramer binding to yeast surface-displaying IIA726 was much lower, suggesting that disulfide bond formation between the BC and DE loops was important for binding activity. After MBP-IIA726 was incubated with 10 μM of $CuSO_4$ for 1 hour at RT (cupric-catalyzed oxidation), the blocking ability was significantly enhanced. MBP-IIA726 was then produced in Rosetta-gami 2, a strain containing mutations to promote disulfide bond formation in the cytosol. The blocking ability of this preparation was high and not significantly improved by incubation with $CuSO_4$.

To determine whether the Fn3 domains were able to recognize FcRs expressed on cell surfaces, each MBP-Fn3 fusion protein was biotinylated, complexed with streptavidin-PE and used to label human peripheral blood mononuclear cells (PBMCs). Since B and T cells do not express RIIA or RIIIA, lymphocytes were excluded by forward and side scatter during flow cytometry analysis. MBP-IIA726 labeled the non-lymphocyte PBMCs more than the control of MBP alone, and a subpopulation of cells were distinctly labeled by MBP-IIIA537 and MBP-IIIA626 (FIG. 1, panel D). Although the shift in fluorescence intensity for MBP-IIA726 was small (not unexpected because of the low avidity of streptavidin complexes), it was unlikely to be non-specific because no such shift was observed with the lymphocytes.

These three MBP-Fn3 fusion proteins as well as MBP-IIA827 (also produced in Rosetta-gami 2) were subjected to Surface Plasmon Resonance (SPR) analysis, according to the method in Example 1, to determine the monovalent dissociation constants for the FcRs (Table 2). MBP-IIIA537 and MBP-IIA626 each had single-digit micromolar affinities for their respective antigens, similar to the affinity of IgG1 for the activating FcRs, whereas MBP-IIIA626 and MBP-IIA827 (for RIIA 131R) had sub-micromolar dissociation constants. The RIIIA binders showed no binding to RIIA and RIIB, and the RIIA binders were also highly selective for RIIA over RIIB. Except for MBP-IIA827, the proteins had similar affinities for the two tested isoforms of their target FcR.

TABLE 2

Dissociation constants of MBP-Fn3 fusion proteins for FcRs.

| | $K_d$ (μM) for FcR | | | | |
|---|---|---|---|---|---|
| Protein | RIIA131H | RIIA131R | RIIB | RIIIA 158F176F | RIIIA 158F 176V |
| MBP-IIIA537 | nb | nb | nb | 4.9 | 3.9 |
| MBP-IIIA626 | nb | nb | nb | 0.53 | 0.54 |
| MBP-IIA726 | 3.3 | 3.2 | nb | nb | nb |
| MBP-IIA826 | 6.2 | 0.85 | ud | nb | ud | nb: no binding observed;
ud: binding was too weak for $K_d$ to be determined (>10 μM)

Example 5

Amino Acid Sequence Alignments of Fn3 Mutants

Amino acid sequence alignments of selected Fn3 mutants identified according to the method in Example 1 are shown in FIG. 2. SEQ ID NO: 1 refers to the wild type Fn3 sequence. SEQ ID NOs: 6-15 were selected from the library evolved to bind to FcRIIA; SEQ ID NOs: 16-35 were selected from the library evolved to bind to FcRIIIA The gaps are shown to illustrate the positions where deletions can be introduced into the wild type sequence but, of course, in reality the amino acid residues are contiguous and connected. Each SEQ ID NO refers to the contiguous sequence. The boldfaced, underlined regions at amino acids 23-30, 52-57 and 77-86 in SEQ ID NO: 1 indicate the positions of the BC loop, the DE loop and the FG loop, respectively. Mutant amino acids are indicated by shading.

A number of embodiments of the invention have been described. Nevertheless, it will be understood that various modifications may be made without departing from the spirit and scope of the invention. Accordingly, other embodiments are within the scope of the following claims.

What is claimed is:

1. An engineered protein comprising a first polypeptide that specifically binds a cellular target and a second polypeptide that specifically binds an activating Fc gamma receptor IIA or IIIA, wherein the second polypeptide comprises a variant fibronectin 3 (Fn3) domain amino acid sequence that is at least 70% identical to SEQ ID NO:1, and wherein the variant Fn3 domain comprises a BC domain, a DE domain, and a FG domain, and wherein at least six of the eight amino acids in the BC domain are substituted or deleted, relative to SEQ ID NO:1.

2. The engineered protein of claim 1, wherein the second polypeptide has an affinity for the activating Fc receptor of about 100 nM.

3. The engineered protein of claim 1, wherein the first polypeptide comprises an immunoglobulin or an antigen-binding fragment thereof.

4. The engineered protein of claim 3, wherein the immunoglobulin is an immunoglobulin of the G class (IgG).

5. The engineered protein of claim 4, wherein the IgG is an IgG1.

6. The engineered protein of claim 1, wherein the first polypeptide is a human polypeptide.

7. The engineered protein of claim 3, wherein the immunoglobulin is a human or humanized immunoglobulin.

8. The engineered protein of claim 1, wherein the cellular target is a cancer antigen.

9. The engineered protein of claim 3, wherein the immunoglobulin is abciximab, adalimumab, alemtuzumab, basiliximab, bevacizumab, certuximab, certolizumab pegol, daclizumab, eculizumab, efalizumab, gemtuzumab, ibrutumomab tiuxetan, Infliximab, muromonab-CD3, natalizumab, omalizumab, palivizumab, panitumumab, ranibizumab, rituximab, tositumomab, or trastuzumab.

10. The engineered protein of claim 9, wherein the second polypeptide is covalently bound to the carboxy terminus of the immunoglobulin or the antigen binding fragment thereof.

11. A nucleic acid comprising a sequence encoding the engineered protein of claim 1.

12. An expression vector comprising the nucleic acid of claim 11 and a regulatory sequence.

13. An isolated host cell comprising the expression vector of claim 12.

14. A pharmaceutical composition comprising the engineered protein of claim 1.

15. A method of treating a patient diagnosed as having cancer, the method comprising administering to the patient the engineered protein of claim 1, wherein the first polypeptide is an immunoglobulin or antigen-binding fragment thereof that specifically binds a cell surface cancer antigen expressed in the patient, wherein the immunoglobulin or antigen-binding fragment thereof is conjugated to a cytotoxic agent.

16. The engineered protein of claim 1, wherein at least three of the five amino acid residues of the DE loop are substituted or deleted and at least eight of the ten amino acid residues of the FG loop are substituted or deleted, relative to SEQ ID NO:1.

17. The engineered protein of claim 1, wherein the BC, DE, and FG domains of the variant Fn3 domain comprise the amino acid sequences:
   a) SEQ ID NO: 39, SEQ ID NO: 46, and SEQ ID NO: 50, respectively;
   b) amino acids 23-27 of SEQ ID NO: 4, amino acids 51-55 of SEQ ID NO: 4, and amino acids 76-81 of SEQ ID NO: 4, respectively;
   c) conservative amino acid substitutions to SEQ ID NO: 39, SEQ ID NO: 46, and SEQ ID NO: 50, respectively; or
   d) conservative amino acid substitutions to amino acids 23-27 of SEQ ID NO: 4, amino acids 51-55 of SEQ ID NO: 4, and amino acids 76-81 of SEQ ID NO: 4, respectively.

18. A protein comprising a variant fibronectin 3 (Fn3) domain amino acid sequence that is at least 70% identical to SEQ ID NO:1 and specifically binds an activating Fc gamma receptor IIA or IIIA, wherein the variant Fn3 domain comprises a BC domain, a DE domain, and a FG domain comprising the amino acid sequences:
   a) SEQ ID NO: 39, SEQ ID NO: 46, and SEQ ID NO: 50, respectively;
   b) amino acids 23-27 of SEQ ID NO: 4, amino acids 51-55 of SEQ ID NO: 4, and amino acids 76-81 of SEQ ID NO: 4, respectively;
   c) conservative amino acid substitutions to SEQ ID NO: 39, SEQ ID NO: 46, and SEQ ID NO: 50, respectively; or
   d) conservative amino acid substitutions to amino acids 23-27 of SEQ ID NO: 4, amino acids 51-55 of SEQ ID NO: 4, and amino acids 76-81 of SEQ ID NO: 4, respectively.

19. A fusion protein comprising the protein of claim 18 linked to the C-terminus of a heterologous amino acid sequence that specifically binds a cellular target other than activating Fc gamma receptor IIA or IIIA.

20. The fusion protein of claim 19, wherein the heterologous amino acid sequence comprises the antigen-binding fragment of an antibody.

21. An engineered protein comprising a first polypeptide that specifically binds a cellular target and a second polypeptide that specifically binds an activating Fc gamma receptor IIA or IIIA, wherein the second polypeptide is selected from the group consisting of SEQ ID NOs: 2-35.

22. The engineered protein of claim 21, wherein the first polypeptide comprises an immunoglobulin or an antigen-binding fragment thereof.

23. The engineered protein of claim 22 wherein the immunoglobulin is a human or humanized immunoglobulin.

24. The engineered protein of claim 22, wherein the immunoglobulin is abciximab, adalimumab, alemtuzumab, basiliximab, bevacizumab, certuximab, certolizumab pegol, daclizumab, eculizumab, efalizumab, gemtuzumab, ibrutumomab tiuxetan, Infliximab, muromonab-CD3, natalizumab, omalizumab, palivizumab, panitumumab, ranibizumab, rituximab, tositumomab, or trastuzumab.

25. The engineered protein of claim 21, wherein the second polypeptide is SEQ ID NO: 2.

26. The engineered protein of claim 21 wherein the second polypeptide is SEQ ID NO: 3.

27. The engineered protein of claim 21 wherein the second polypeptide is SEQ ID NO: 4.

28. The engineered protein of claim 21, wherein the second polypeptide is SEQ ID NO: 5.

* * * * *

SEQUENCE LISTING

<160> NUMBER OF SEQ ID NOS: 60

<210> SEQ ID NO 1

```
<211> LENGTH: 101
<212> TYPE: PRT
<213> ORGANISM: Homo sapiens

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys Pro Ser Gln
            100

<210> SEQ ID NO 2
<211> LENGTH: 96
<212> TYPE: PRT
<213> ORGANISM: Homo sapiens

<400> SEQUENCE: 2

Val Ser Asp Val Pro Arg Asp Leu Glu Val Val Ala Thr Pro Thr
1               5                   10                  15

Ser Leu Leu Ile Asn Trp Asp Leu Pro Phe Ser Asp Ser Tyr Arg Ile
            20                  25                  30

Thr Tyr Gly Glu Thr Gly Gly Asn Ser Pro Val Gln Gly Phe Thr Val
        35                  40                  45

Pro Gly Thr Glu Ser Ile Ala Thr Ile Ser Gly Leu Lys Pro Gly Val
        50                  55                  60

Asp Tyr Thr Ile Thr Val Tyr Ala Val Ala Ser Ser Gly Ser Asn Ser
65                  70                  75                  80

Tyr Pro Ile Ser Ile Asn Tyr Arg Thr Glu Ile Asp Lys Pro Ser Gln
                85                  90                  95

<210> SEQ ID NO 3
<211> LENGTH: 96
<212> TYPE: PRT
<213> ORGANISM: Homo sapiens

<400> SEQUENCE: 3

Val Ser Asp Val Pro Arg Asp Leu Glu Val Val Ala Thr Pro Thr
1               5                   10                  15

Ser Leu Leu Ile Asn Trp Asp Met Pro Phe Ser Asp Ser Tyr Arg Ile
            20                  25                  30

Ala Tyr Gly Glu Thr Gly Gly Asn Ser Pro Val Gln Glu Phe Thr Val
        35                  40                  45

Pro Gly Thr Asp Ser Leu Ala Thr Ile Ser Gly Leu Lys Pro Gly Val
        50                  55                  60

Asp Tyr Thr Ile Thr Val Tyr Ala Val Thr Ser Ser Gly Ser Asn Ser
65                  70                  75                  80

Tyr Pro Ile Ser Ile Asn Tyr Arg Thr Glu Ile Asp Lys Pro Ser Gln
                85                  90                  95
```

```
<210> SEQ ID NO 4
<211> LENGTH: 96
<212> TYPE: PRT
<213> ORGANISM: Homo sapiens

<400> SEQUENCE: 4

Val Ser Asp Val Pro Gly Asp Leu Glu Val Val Ala Ala Thr Pro Thr
 1               5                  10                  15

Ser Leu Leu Ile Ser Trp Cys Thr His Leu His Trp Asp Tyr Tyr Arg
            20                  25                  30

Ile Phe Tyr Gly Glu Thr Gly Gly Asn Ser Pro Val Gln Glu Phe Thr
        35                  40                  45

Val Pro Ala Leu Cys Pro Gly Ala Thr Ile Ser Gly Leu Lys Pro Gly
50                  55                  60

Val Asp Tyr Thr Ile Thr Ala Tyr Ala Val Thr Val Gly Gly Asp Asp
65                  70                  75                  80

Trp Pro Ile Ser Ile Asn Tyr Arg Thr Glu Ile Asp Glu Pro Ser Gln
                85                  90                  95

<210> SEQ ID NO 5
<211> LENGTH: 96
<212> TYPE: PRT
<213> ORGANISM: Homo sapiens

<400> SEQUENCE: 5

Val Ser Asp Val Pro Gly Asp Leu Glu Val Val Ala Ala Thr Pro Thr
 1               5                  10                  15

Ser Leu Leu Ile Ser Trp Cys Thr His Leu His Trp Asp Tyr Tyr Arg
            20                  25                  30

Ile Phe Tyr Gly Glu Thr Gly Gly Asn Ser Pro Val Gln Glu Phe Thr
        35                  40                  45

Val Pro Ala Leu Cys Pro Gly Ala Thr Ile Ser Gly Leu Lys Pro Gly
50                  55                  60

Val Asp Tyr Thr Ile Thr Ala Tyr Ala Val Thr Val Gly Gly Asp Asp
65                  70                  75                  80

Trp Pro Ser Ser Ile Asn Tyr Arg Thr Glu Ile Asp Glu Pro Ser Gln
                85                  90                  95

<210> SEQ ID NO 6
<211> LENGTH: 96
<212> TYPE: PRT
<213> ORGANISM: Homo sapiens

<400> SEQUENCE: 6

Val Ser Asp Val Ser Arg Asp Leu Glu Val Val Ala Ala Thr Pro Thr
 1               5                  10                  15

Ser Leu Leu Ile Ser Trp Cys Thr His Leu His Arg Asp Tyr Tyr Arg
            20                  25                  30

Ile Thr Tyr Gly Glu Thr Gly Gly Asn Ser Pro Val Gln Glu Phe Thr
        35                  40                  45

Val Pro Ala Leu Cys Pro Gly Ala Thr Ile Ser Gly Leu Lys Pro Gly
50                  55                  60

Val Gly Tyr Thr Ile Thr Val Tyr Ala Val Thr Val Gly Glu Asp Val
65                  70                  75                  80

Trp Ser Ile Ser Ile Asn Tyr Leu Ala Glu Ile Asp Lys Pro Phe Gln
                85                  90                  95

<210> SEQ ID NO 7
<211> LENGTH: 96
```

```
<212> TYPE: PRT
<213> ORGANISM: Homo sapiens

<400> SEQUENCE: 7

Val Ser Asp Val Ser Arg Asp Leu Glu Val Ala Ala Thr Pro Thr
1               5                   10                  15

Ser Leu Leu Ile Ser Trp Cys Thr His Leu His Arg Asp Tyr Tyr Arg
            20                  25                  30

Ile Thr Tyr Gly Glu Thr Gly Gly Asn Ser Pro Val Gln Glu Phe Thr
            35                  40                  45

Val Pro Ala Leu Cys Pro Gly Ala Thr Ile Ser Gly Leu Lys Pro Gly
            50                  55                  60

Val Gly Tyr Thr Ile Thr Val Tyr Ala Val Thr Val Gly Glu Asp Val
65              70                  75                  80

Trp Ser Ile Ser Ile Asn Tyr Leu Ala Glu Ile Asp Glu Pro Phe Gln
                85                  90                  95

<210> SEQ ID NO 8
<211> LENGTH: 93
<212> TYPE: PRT
<213> ORGANISM: Homo sapiens

<400> SEQUENCE: 8

Val Ser Asp Val Pro Arg Asp Leu Glu Val Val Ala Ala Thr Pro Thr
1               5                   10                  15

Ser Leu Leu Ile Ser Trp Ala Met Asp Lys Ala Leu Tyr Tyr Arg Ile
            20                  25                  30

Thr Tyr Gly Glu Thr Gly Gly Asn Ser Pro Val Gln Glu Phe Thr Val
            35                  40                  45

Pro Gly Pro Leu Ser Ala Thr Ile Ser Ala Leu Lys Pro Gly Val Asp
    50                  55                  60

Tyr Thr Ile Thr Val Cys Ala Val Thr Leu Tyr Tyr Asp Tyr Pro Ile
65              70                  75                  80

Ser Ile Asn Tyr Arg Ala Glu Ile Asp Glu Pro Ser Gln
                85                  90

<210> SEQ ID NO 9
<211> LENGTH: 93
<212> TYPE: PRT
<213> ORGANISM: Homo sapiens

<400> SEQUENCE: 9

Val Ser Asp Val Pro Arg Asp Leu Glu Val Val Ala Ala Thr Pro Thr
1               5                   10                  15

Ser Leu Leu Ile Ser Trp Ala Met Asp Lys Ala Leu Tyr Tyr Arg Ile
            20                  25                  30

Thr Tyr Gly Glu Thr Gly Gly Asn Ser Pro Val Gln Glu Phe Thr Val
            35                  40                  45

Pro Gly Pro Leu Ser Thr Thr Ile Ser Ala Leu Lys Pro Gly Val Asp
    50                  55                  60

Tyr Thr Ile Thr Val Tyr Ala Val Thr Leu Tyr Tyr Asp Tyr Pro Ile
65              70                  75                  80

Ser Ile Asn Tyr Arg Pro Glu Ile Asp Glu Pro Ser Gln
                85                  90

<210> SEQ ID NO 10
<211> LENGTH: 96
<212> TYPE: PRT
<213> ORGANISM: Homo sapiens
```

<400> SEQUENCE: 10

Val Ser Asp Val Ser Gly Asp Leu Glu Val Ala Ala Thr Pro Thr
1               5                   10                  15

Ser Leu Leu Ile Ser Trp Cys Thr His Leu His Arg Asp Tyr Tyr Arg
                20                  25                  30

Ile Thr Tyr Gly Glu Thr Gly Gly Asn Ser Pro Val Gln Glu Phe Thr
            35                  40                  45

Val Pro Ala Leu Cys Pro Gly Ala Thr Ile Ser Gly Leu Lys Pro Gly
    50                  55                  60

Val Gly Tyr Thr Ile Thr Val Tyr Ala Val Thr Val Gly Glu Asp Val
65                  70                  75                  80

Trp Ser Ile Ser Ile Asn Tyr Leu Ala Glu Ile Asp Lys Pro Phe Gln
                85                  90                  95

<210> SEQ ID NO 11
<211> LENGTH: 96
<212> TYPE: PRT
<213> ORGANISM: Homo sapiens

<400> SEQUENCE: 11

Val Ser Asp Val Pro Gly Asp Leu Glu Val Ala Ala Thr Pro Thr
1               5                   10                  15

Ser Leu Leu Ile Ser Trp Cys Thr His Leu His Trp Asp Tyr Tyr Arg
                20                  25                  30

Ile Phe Tyr Gly Glu Thr Gly Gly Asn Ser Pro Val Gln Glu Phe Thr
            35                  40                  45

Val Pro Ala Leu Cys Pro Gly Ala Thr Ile Ser Gly Leu Lys Pro Gly
    50                  55                  60

Val Asp Tyr Thr Ile Thr Ala Tyr Ala Val Thr Val Gly Gly Asp Asp
65                  70                  75                  80

Trp Pro Ile Ser Ile Asn Tyr Arg Thr Glu Ile Asp Gly Pro Ser Gln
                85                  90                  95

<210> SEQ ID NO 12
<211> LENGTH: 96
<212> TYPE: PRT
<213> ORGANISM: Homo sapiens

<400> SEQUENCE: 12

Val Ser Asp Val Ser Gly Asp Leu Glu Val Ala Ala Thr Pro Thr
1               5                   10                  15

Ser Leu Leu Ile Ser Trp Cys Thr His Leu His Arg Asp Tyr Tyr Arg
                20                  25                  30

Ile Thr Tyr Gly Glu Thr Gly Gly Asn Ser Pro Val Gln Glu Phe Thr
            35                  40                  45

Val Pro Ala Leu Cys Pro Gly Ala Thr Ile Ser Gly Leu Lys Pro Gly
    50                  55                  60

Val Gly Tyr Thr Ile Thr Val Tyr Ala Val Thr Val Gly Glu Asp Val
65                  70                  75                  80

Trp Ser Ile Ser Ile Asn Tyr Leu Ala Glu Ile Asp Lys Pro Phe Gln
                85                  90                  95

<210> SEQ ID NO 13
<211> LENGTH: 96
<212> TYPE: PRT
<213> ORGANISM: Homo sapiens

<400> SEQUENCE: 13

```
Val Ser Asp Val Ser Arg Asp Leu Glu Val Ala Ala Thr Pro Thr
 1               5                  10                  15

Ser Leu Leu Ile Ser Trp Cys Thr His Leu Arg Arg Asp Tyr Tyr Arg
            20                  25                  30

Ile Thr Tyr Gly Glu Thr Gly Gly Asn Ser Pro Val Gln Glu Phe Thr
            35                  40                  45

Val Pro Ala Leu Cys Pro Gly Ala Thr Ile Ser Gly Leu Lys Pro Gly
 50                  55                  60

Val Gly Tyr Thr Ile Thr Val Tyr Ala Val Thr Val Gly Glu Asp Val
 65                  70                  75                  80

Trp Ser Ile Ser Ile Asn Tyr Leu Thr Glu Ile Asp Glu Pro Ser Gln
                85                  90                  95
```

<210> SEQ ID NO 14
<211> LENGTH: 96
<212> TYPE: PRT
<213> ORGANISM: Homo sapiens

<400> SEQUENCE: 14

```
Val Ser Asp Val Ser Arg Asp Leu Glu Val Ala Ala Thr Pro Thr
 1               5                  10                  15

Ser Leu Leu Ile Ser Trp Cys Thr His Leu His Arg Asp Tyr Tyr Arg
            20                  25                  30

Ile Thr Tyr Gly Glu Thr Gly Gly Ser Ser Pro Val Gln Glu Phe Thr
            35                  40                  45

Val Pro Ala Leu Cys Pro Gly Ala Thr Ile Ser Gly Leu Lys Pro Gly
 50                  55                  60

Val Gly Tyr Thr Ile Thr Val Tyr Ala Val Thr Val Gly Glu Asp Val
 65                  70                  75                  80

Trp Ser Ile Ser Ile Asn Tyr Leu Ala Glu Ile Asp Glu Pro Phe Gln
                85                  90                  95
```

<210> SEQ ID NO 15
<211> LENGTH: 93
<212> TYPE: PRT
<213> ORGANISM: Homo sapiens

<400> SEQUENCE: 15

```
Val Ser Asp Ala Pro Arg Asp Leu Glu Val Ala Glu Thr Pro Thr
 1               5                  10                  15

Ser Leu Leu Ile Ser Trp Ala Met Asp Lys Ala Leu Tyr Tyr Arg Ile
            20                  25                  30

Thr Tyr Gly Glu Thr Gly Gly Asn Ser Pro Val Gln Glu Phe Thr Val
            35                  40                  45

Pro Gly Pro Leu Ser Ala Thr Ile Ser Ala Leu Lys Pro Gly Val Asp
 50                  55                  60

Tyr Thr Ile Thr Val Tyr Ala Val Thr Leu Tyr Tyr Pro Tyr Pro Ile
 65                  70                  75                  80

Ser Ile Asn Tyr Arg Pro Glu Ile Asp Glu Pro Ser Gln
                85                  90
```

<210> SEQ ID NO 16
<211> LENGTH: 96
<212> TYPE: PRT
<213> ORGANISM: Homo sapiens

<400> SEQUENCE: 16

```
Val Ser Asp Val Pro Arg Asp Leu Glu Val Ile Ala Ala Thr Pro Thr
```

```
                1               5                  10                 15
Ser Leu Leu Ile Asn Trp Asp Leu Pro Phe Ser Asn Ser Tyr Arg Ile
                    20                  25                  30

Thr Tyr Gly Glu Thr Gly Gly Asn Ser Pro Val Gln Glu Phe Thr Val
            35                  40                  45

Pro Gly Thr Asp Ser Ile Ala Thr Ile Ser Gly Leu Lys Pro Gly Val
        50                  55                  60

Asp Tyr Thr Ile Thr Val Tyr Ala Val Thr Ser Ser Gly Ser Asn Ser
65                  70                  75                  80

Tyr Pro Ile Ser Ile Asn Tyr Arg Thr Glu Ile Asp Lys Pro Ser Gln
                    85                  90                  95
```

<210> SEQ ID NO 17
<211> LENGTH: 96
<212> TYPE: PRT
<213> ORGANISM: Homo sapiens

<400> SEQUENCE: 17

```
Val Ser Asp Val Pro Arg Gly Leu Glu Val Val Ala Ala Thr Pro Thr
1               5                   10                  15

Ser Leu Leu Ile Asn Trp Asp Met Pro Phe Ser Asp Ser Tyr Arg Ile
                    20                  25                  30

Thr Tyr Gly Glu Thr Gly Gly Asn Ser Pro Val Gln Glu Phe Thr Val
            35                  40                  45

Pro Gly Thr Asp Ser Ile Ala Thr Ile Ser Gly Leu Lys Pro Gly Val
        50                  55                  60

Asp Tyr Thr Ile Thr Val Tyr Ala Val Thr Ser Ser Gly Ser Asn Ser
65                  70                  75                  80

Tyr Pro Ile Ser Ile Asn Tyr Arg Thr Glu Ile Asn Lys Pro Ser Gln
                    85                  90                  95
```

<210> SEQ ID NO 18
<211> LENGTH: 96
<212> TYPE: PRT
<213> ORGANISM: Homo sapiens

<400> SEQUENCE: 18

```
Val Ser Asp Val Pro Arg Gly Leu Glu Val Val Ala Ala Thr Pro Thr
1               5                   10                  15

Ser Leu Leu Ile Asn Trp Asp Met Pro Phe Ser Asp Ser Tyr Arg Ile
                    20                  25                  30

Thr Tyr Gly Glu Thr Gly Gly Asn Ser Pro Val Gln Glu Phe Thr Val
            35                  40                  45

Pro Gly Thr Asp Ser Ile Ala Thr Ile Ser Gly Leu Lys Pro Gly Val
        50                  55                  60

Asp Tyr Thr Ile Thr Val Tyr Ala Val Thr Ser Ser Gly Ser Asn Ser
65                  70                  75                  80

Tyr Pro Ile Ser Ile Asn Tyr Arg Thr Glu Val Asp Lys Pro Ser Gln
                    85                  90                  95
```

<210> SEQ ID NO 19
<211> LENGTH: 96
<212> TYPE: PRT
<213> ORGANISM: Homo sapiens

<400> SEQUENCE: 19

```
Val Pro Asp Val Pro Arg Asp Leu Glu Val Val Ala Ala Thr Pro Thr
1               5                   10                  15
```

```
Ser Leu Leu Ile Asn Trp Asp Met Pro Phe Ser Asp Ser Tyr Arg Ile
            20                  25                  30

Thr Tyr Gly Glu Thr Gly Gly Asn Ser Pro Val Gln Glu Phe Thr Val
            35                  40                  45

Pro Gly Thr Asp Ser Ile Ala Thr Ile Ser Gly Leu Lys Pro Gly Val
 50                  55                  60

Asp Tyr Thr Ile Thr Val Tyr Ala Val Thr Ser Ser Gly Ser Asn Ser
 65                  70                  75                  80

Tyr Pro Ile Ser Ile Asn Tyr Arg Thr Glu Val Asp Lys Pro Ser Gln
                85                  90                  95

<210> SEQ ID NO 20
<211> LENGTH: 96
<212> TYPE: PRT
<213> ORGANISM: Homo sapiens

<400> SEQUENCE: 20

Val Ser Asp Val Pro Arg Asp Leu Glu Val Val Ala Ala Thr Pro Thr
  1               5                  10                  15

Ser Leu Leu Ile Asn Trp Asp Leu Pro Phe Ser Asp Ser Tyr Arg Ile
            20                  25                  30

Thr Tyr Gly Glu Thr Gly Gly Asn Ser Pro Val Gln Glu Phe Thr Val
            35                  40                  45

Pro Gly Thr Asp Ser Ile Ala Thr Ile Ser Gly Leu Lys Pro Gly Val
 50                  55                  60

Asp Tyr Thr Ile Thr Val Tyr Ala Val Thr Ser Ser Gly Ser Asn Ser
 65                  70                  75                  80

Tyr Pro Val Ser Val Asn Tyr Arg Thr Glu Ile Asp Lys Pro Ser Arg
                85                  90                  95

<210> SEQ ID NO 21
<211> LENGTH: 96
<212> TYPE: PRT
<213> ORGANISM: Homo sapiens

<400> SEQUENCE: 21

Val Ser Asp Val Pro Arg Asp Leu Glu Val Val Ala Ala Thr Pro Thr
  1               5                  10                  15

Ser Leu Leu Ile Asn Trp Asp Leu Pro Phe Ser Asp Ser Tyr Arg Ile
            20                  25                  30

Thr Tyr Gly Glu Thr Gly Gly Asn Ser Pro Val Gln Glu Phe Thr Val
            35                  40                  45

Pro Gly Ile Asp Ser Ile Ala Thr Ile Ser Gly Leu Lys Pro Gly Val
 50                  55                  60

Asp Tyr Thr Ile Thr Val Tyr Ala Val Thr Ser Ser Gly Ser Asn Ser
 65                  70                  75                  80

Tyr Pro Ile Ser Ile Asn Tyr Arg Thr Glu Ile Asp Lys Pro Ser Gln
                85                  90                  95

<210> SEQ ID NO 22
<211> LENGTH: 96
<212> TYPE: PRT
<213> ORGANISM: Homo sapiens

<400> SEQUENCE: 22

Val Ser Asp Val Pro Arg Asp Leu Glu Val Val Ala Ala Thr Pro Thr
  1               5                  10                  15

Ser Leu Leu Ile Asn Trp Asp Leu Pro Phe Ser Asp Ser Tyr Arg Ile
            20                  25                  30
```

```
Thr Tyr Gly Glu Thr Gly Gly Asn Ser Pro Val Gln Gly Phe Thr Val
            35                  40                  45

Pro Gly Thr Glu Ser Ile Ala Thr Ile Ser Gly Leu Lys Pro Gly Val
 50                  55                  60

Asp Tyr Thr Ile Thr Val Tyr Ala Val Ala Ser Gly Ser Asn Ser
 65                  70                  75                  80

Tyr Pro Ile Ser Ile Asn Tyr Arg Thr Glu Ile Asp Lys Pro Ser Gln
            85                  90                  95
```

<210> SEQ ID NO 23
<211> LENGTH: 90
<212> TYPE: PRT
<213> ORGANISM: Homo sapiens

<400> SEQUENCE: 23

```
Val Ser Asp Val Pro Arg Asp Leu Glu Val Val Ala Ala Thr Pro Thr
  1               5                  10                  15

Ser Leu Leu Ile Asn Trp Asp Leu Pro Phe Ser Asp Ser Tyr Arg Ile
             20                  25                  30

Thr Tyr Gly Gly Thr Gly Gly Asn Ser Pro Val Gln Glu Phe Thr Val
            35                  40                  45

Pro Gly Thr Asp Ser Ile Ala Thr Ile Ser Gly Leu Lys Pro Gly Val
 50                  55                  60

Asp Tyr Thr Ile Thr Val Tyr Ala Val Thr Ser Asn Gly Leu Val Pro
 65                  70                  75                  80

Ile Ser Thr Asn Tyr Arg Thr Glu Ile Asp
            85                  90
```

<210> SEQ ID NO 24
<211> LENGTH: 96
<212> TYPE: PRT
<213> ORGANISM: Homo sapiens

<400> SEQUENCE: 24

```
Val Ser Asp Val Pro Arg Asp Leu Glu Val Val Ala Ala Thr Pro Thr
  1               5                  10                  15

Ser Leu Leu Ile Asn Trp Asp Leu Pro Phe Ser Asp Ser Tyr Arg Ile
             20                  25                  30

Thr Tyr Gly Glu Thr Gly Gly Asn Ser Pro Val Gln Glu Phe Thr Val
            35                  40                  45

Pro Gly Thr Asp Ser Ile Ala Thr Ile Ser Gly Leu Lys Pro Gly Val
 50                  55                  60

Asp Tyr Thr Ile Thr Val Tyr Ala Val Thr Ser Ser Gly Ser Asn Ser
 65                  70                  75                  80

Tyr Pro Ile Ser Ile Asn Tyr Arg Thr Glu Ile Asp Lys His Pro Arg
            85                  90                  95
```

<210> SEQ ID NO 25
<211> LENGTH: 96
<212> TYPE: PRT
<213> ORGANISM: Homo sapiens

<400> SEQUENCE: 25

```
Val Ser Asp Val Pro Arg Gly Leu Glu Val Val Ala Ala Thr Pro Thr
  1               5                  10                  15

Ser Leu Leu Ile Asn Trp Asp Leu Pro Phe Ser Asp Ser Tyr Arg Ile
             20                  25                  30

Thr Tyr Gly Glu Thr Gly Gly Asn Ser Pro Val Gln Glu Phe Thr Val
```

```
            35                  40                  45
Pro Gly Thr Asp Ser Leu Ala Thr Val Ser Gly Leu Lys Pro Gly Val
 50                  55                  60

Asp Tyr Thr Ile Thr Val Tyr Ala Val Ala Ser Ser Gly Ser Asn Ser
 65                  70                  75                  80

Tyr Pro Ile Ser Ile Asn Tyr Arg Thr Glu Ile Asp Lys Pro Ser Gln
                 85                  90                  95

<210> SEQ ID NO 26
<211> LENGTH: 96
<212> TYPE: PRT
<213> ORGANISM: Homo sapiens

<400> SEQUENCE: 26

Val Ser Asp Val Pro Arg Gly Leu Glu Val Leu Val Ala Thr Pro Thr
 1               5                  10                  15

Ser Leu Leu Ile Asn Trp Asp Leu Pro Phe Ser Asp Ser Tyr Arg Ile
                 20                  25                  30

Thr Tyr Gly Glu Thr Gly Gly Asn Ser Pro Val Gln Glu Phe Thr Val
             35                  40                  45

Pro Gly Thr Asp Ser Ile Ala Thr Ile Ser Gly Leu Lys Pro Gly Val
 50                  55                  60

Asp Tyr Thr Val Thr Val Tyr Ala Val Thr Ser Ser Gly Ser Asn Ser
 65                  70                  75                  80

Tyr Pro Ile Ser Ile Asn Tyr Arg Thr Glu Ala Asp Lys Pro Ser Gln
                 85                  90                  95

<210> SEQ ID NO 27
<211> LENGTH: 96
<212> TYPE: PRT
<213> ORGANISM: Homo sapiens

<400> SEQUENCE: 27

Val Ser Asp Val Pro Arg Gly Leu Glu Val Val Ala Ala Thr Pro Thr
 1               5                  10                  15

Ser Leu Leu Ile Asn Trp Asp Leu Pro Phe Ser Asp Ser Tyr Arg Ile
                 20                  25                  30

Thr Tyr Gly Glu Thr Gly Gly Asn Ser Pro Val Gln Glu Ile Thr Met
             35                  40                  45

Pro Gly Thr Asp Ser Ile Ala Thr Ile Ser Gly Leu Lys Pro Gly Val
 50                  55                  60

Asp Tyr Thr Ile Thr Val Tyr Ala Val Thr Ser Ser Gly Ser Asn Ser
 65                  70                  75                  80

Tyr Pro Ile Ser Ile Asn Ser Arg Thr Glu Ile Asp Arg Pro Ser Gln
                 85                  90                  95

<210> SEQ ID NO 28
<211> LENGTH: 96
<212> TYPE: PRT
<213> ORGANISM: Homo sapiens

<400> SEQUENCE: 28

Val Ser Asp Val Pro Arg Gly Leu Glu Val Val Ala Ala Thr Pro Thr
 1               5                  10                  15

Ser Leu Leu Ile Asn Trp Asp Met Pro Phe Ser Asp Ser Tyr Arg Ile
                 20                  25                  30

Thr Tyr Gly Glu Thr Gly Gly Asn Ser Pro Val Arg Glu Phe Thr Ala
             35                  40                  45
```

```
Pro Gly Thr Asp Ser Ile Ala Thr Ile Ser Gly Leu Lys Pro Gly Val
            50                   55                  60

Asp Tyr Thr Ile Thr Val Tyr Ala Val Thr Ser Gly Gly Phe Asn Ser
 65                  70                  75                  80

Tyr Pro Ile Ser Ile Asn Tyr Arg Thr Glu Ile Asp Lys Pro Ser Gln
                85                  90                  95

<210> SEQ ID NO 29
<211> LENGTH: 96
<212> TYPE: PRT
<213> ORGANISM: Homo sapiens

<400> SEQUENCE: 29

Val Ser Asp Val Pro Arg Gly Leu Glu Val Val Ala Thr Pro Thr
 1               5                  10                  15

Ser Leu Leu Ile Asn Trp Asp Met Pro Phe Ser Asp Ser Tyr Arg Ile
                20                  25                  30

Thr Tyr Gly Glu Thr Gly Gly Asn Ser Pro Val Gln Glu Phe Thr Val
                35                  40                  45

Pro Gly Thr Glu Ser Ile Ala Thr Ile Ser Gly Leu Lys Pro Gly Val
            50                   55                  60

Asp Tyr Thr Ile Thr Val Tyr Ala Val Thr Ser Ser Gly Ser Asn Ser
 65                  70                  75                  80

Tyr Pro Ile Ser Ile Asn Tyr Arg Thr Glu Ile Asp Lys Pro Ser Gln
                85                  90                  95

<210> SEQ ID NO 30
<211> LENGTH: 96
<212> TYPE: PRT
<213> ORGANISM: Homo sapiens

<400> SEQUENCE: 30

Val Ser Asp Val Pro Arg Gly Leu Glu Val Val Ala Thr Pro Thr
 1               5                  10                  15

Ser Leu Leu Ile Asn Trp Asp Met Pro Phe Ser Asp Ser Tyr Arg Ile
                20                  25                  30

Thr Tyr Gly Glu Thr Gly Gly Asn Ser Pro Val Gln Glu Phe Thr Val
                35                  40                  45

Pro Gly Thr Asp Ser Ile Ala Thr Ile Ser Gly Leu Lys Pro Gly Val
            50                   55                  60

Asp Tyr Thr Ile Thr Val Tyr Ala Val Thr Ser Ser Gly Ser Asn Ser
 65                  70                  75                  80

Tyr Pro Ile Ser Ile Asn Tyr Arg Thr Glu Ile Asp Lys Pro Ser Gln
                85                  90                  95

<210> SEQ ID NO 31
<211> LENGTH: 96
<212> TYPE: PRT
<213> ORGANISM: Homo sapiens

<400> SEQUENCE: 31

Val Ser Asp Val Pro Arg Asp Leu Glu Val Val Ala Thr Pro Thr
 1               5                  10                  15

Ser Leu Leu Ile Asn Trp Asp Met Pro Phe Ser Asp Ser Tyr Arg Ile
                20                  25                  30

Ala Tyr Gly Glu Thr Gly Gly Asn Ser Pro Val Gln Glu Phe Thr Val
                35                  40                  45

Pro Gly Thr Asp Ser Leu Ala Thr Ile Ser Gly Leu Lys Pro Gly Val
            50                   55                  60
```

Asp Tyr Thr Ile Thr Val Tyr Ala Val Thr Ser Ser Gly Ser Asn Ser
65                  70                  75                  80

Tyr Pro Ile Ser Ile Asn Tyr Arg Thr Glu Ile Asp Lys Pro Ser Gln
                85                  90                  95

<210> SEQ ID NO 32
<211> LENGTH: 96
<212> TYPE: PRT
<213> ORGANISM: Homo sapiens

<400> SEQUENCE: 32

Val Ser Asp Val Pro Arg Gly Leu Glu Val Val Ala Thr Pro Thr
1               5                   10                  15

Ser Leu Leu Ile Asn Trp Asp Met Pro Phe Ser Asp Ser Tyr Arg Ile
                20                  25                  30

Thr Tyr Gly Glu Thr Gly Gly Asn Ser Pro Val Gln Glu Phe Thr Val
            35                  40                  45

Pro Gly Thr Asp Ser Ile Ala Thr Ile Ser Gly Leu Glu Pro Gly Val
        50                  55                  60

Asp Tyr Thr Ile Thr Val Tyr Ala Val Ala Ser Ser Gly Ser Asn Ser
65                  70                  75                  80

Tyr Pro Ile Ser Ile Asn Tyr Arg Thr Glu Ile Asp Lys Pro Thr Gln
                85                  90                  95

<210> SEQ ID NO 33
<211> LENGTH: 96
<212> TYPE: PRT
<213> ORGANISM: Homo sapiens

<400> SEQUENCE: 33

Val Ser Asp Val Pro Arg Gly Leu Glu Val Leu Ala Ala Ala Pro Thr
1               5                   10                  15

Ser Leu Leu Ile Asn Trp Asp Met Pro Phe Ser Asp Ser Tyr Arg Ile
                20                  25                  30

Thr Tyr Gly Glu Thr Gly Gly Asn Ser Pro Val Gln Glu Phe Thr Val
            35                  40                  45

Pro Gly Thr Asp Ser Ile Ala Thr Ile Ser Gly Leu Lys Pro Gly Val
        50                  55                  60

Asp Tyr Thr Ile Thr Val Tyr Ala Val Thr Ser Ser Gly Ser Ser Ser
65                  70                  75                  80

Tyr Pro Ile Ser Ile Asn Tyr Arg Thr Glu Ile Asp Lys Pro Ser Gln
                85                  90                  95

<210> SEQ ID NO 34
<211> LENGTH: 96
<212> TYPE: PRT
<213> ORGANISM: Homo sapiens

<400> SEQUENCE: 34

Val Ser Asp Val Pro Arg Gly Leu Glu Val Ala Ala Thr Pro Thr
1               5                   10                  15

Ser Leu Leu Ile Asn Trp Asp Met Pro Phe Ser Asp Ser Tyr Arg Ile
                20                  25                  30

Thr Tyr Gly Glu Thr Gly Gly Asn Ser Pro Val Gln Glu Phe Ala Ala
            35                  40                  45

Pro Gly Thr Asp Ser Ile Ala Thr Ile Ser Gly Leu Lys Pro Gly Val
        50                  55                  60

Asp Tyr Thr Ile Thr Val Tyr Ala Val Thr Ser Ser Gly Ser Asn Ser

```
                65                  70                  75                  80
Tyr Pro Ile Ser Ile Asn Tyr Arg Thr Glu Ile Asp Lys Pro Ser Gln
                85                  90                  95

<210> SEQ ID NO 35
<211> LENGTH: 96
<212> TYPE: PRT
<213> ORGANISM: Homo sapiens

<400> SEQUENCE: 35

Val Ser Asp Val Pro Arg Asp Leu Glu Val Ile Val Ala Thr Pro Thr
1               5                   10                  15

Ser Leu Leu Ile Asn Trp Asp Met Pro Phe Ser Asp Ser Tyr Arg Ile
                20                  25                  30

Thr Tyr Gly Glu Thr Gly Gly Asn Ser Pro Val Gln Glu Phe Thr Val
            35                  40                  45

Pro Gly Thr Asp Ser Ile Ala Thr Ile Ser Gly Leu Lys Pro Gly Val
        50                  55                  60

Asp Tyr Thr Ile Thr Val Tyr Ala Val Thr Ser Ser Gly Ser Asn Ser
65                  70                  75                  80

Tyr Pro Ile Ser Ile Asn Tyr Arg Thr Glu Ile Asp Lys Pro Pro Gln
                85                  90                  95

<210> SEQ ID NO 36
<211> LENGTH: 7
<212> TYPE: PRT
<213> ORGANISM: Homo sapiens

<400> SEQUENCE: 36

Cys Thr His Leu His Arg Asp
1               5

<210> SEQ ID NO 37
<211> LENGTH: 6
<212> TYPE: PRT
<213> ORGANISM: Homo sapiens

<400> SEQUENCE: 37

Ala Met Asp Lys Ala Leu
1               5

<210> SEQ ID NO 38
<211> LENGTH: 7
<212> TYPE: PRT
<213> ORGANISM: Homo sapiens

<400> SEQUENCE: 38

Asp Leu Pro Phe Ser Asp Ser
1               5

<210> SEQ ID NO 39
<211> LENGTH: 7
<212> TYPE: PRT
<213> ORGANISM: Homo sapiens

<400> SEQUENCE: 39

Asp Met Pro Phe Ser Asp Ser
1               5

<210> SEQ ID NO 40
<211> LENGTH: 7
<212> TYPE: PRT
<213> ORGANISM: Homo sapiens
```

<400> SEQUENCE: 40

Asp Leu Pro Phe Ser Asp Ser
1               5

<210> SEQ ID NO 41
<211> LENGTH: 5
<212> TYPE: PRT
<213> ORGANISM: Homo sapiens

<400> SEQUENCE: 41

Ala Leu Cys Pro Gly
1               5

<210> SEQ ID NO 42
<211> LENGTH: 5
<212> TYPE: PRT
<213> ORGANISM: Homo sapiens

<400> SEQUENCE: 42

Gly Pro Leu Ser Ala
1               5

<210> SEQ ID NO 43
<211> LENGTH: 5
<212> TYPE: PRT
<213> ORGANISM: Homo sapiens

<400> SEQUENCE: 43

Gly Pro Leu Ser Thr
1               5

<210> SEQ ID NO 44
<211> LENGTH: 5
<212> TYPE: PRT
<213> ORGANISM: Homo sapiens

<400> SEQUENCE: 44

Gly Thr Asp Ser Ile
1               5

<210> SEQ ID NO 45
<211> LENGTH: 5
<212> TYPE: PRT
<213> ORGANISM: Homo sapiens

<400> SEQUENCE: 45

Gly Thr Glu Ser Ile
1               5

<210> SEQ ID NO 46
<211> LENGTH: 5
<212> TYPE: PRT
<213> ORGANISM: Homo sapiens

<400> SEQUENCE: 46

Gly Thr Asp Ser Leu
1               5

<210> SEQ ID NO 47
<211> LENGTH: 7
<212> TYPE: PRT
<213> ORGANISM: Homo sapiens

<400> SEQUENCE: 47

```
Val Gly Glu Asp Val Trp Ser
1               5

<210> SEQ ID NO 48
<211> LENGTH: 5
<212> TYPE: PRT
<213> ORGANISM: Homo sapiens

<400> SEQUENCE: 48

Leu Tyr Tyr Asp Tyr
1               5

<210> SEQ ID NO 49
<211> LENGTH: 7
<212> TYPE: PRT
<213> ORGANISM: Homo sapiens

<400> SEQUENCE: 49

Val Gly Glu Asp Val Trp Ser
1               5

<210> SEQ ID NO 50
<211> LENGTH: 5
<212> TYPE: PRT
<213> ORGANISM: Homo sapiens

<400> SEQUENCE: 50

Ser Ser Gly Ser Asn
1               5

<210> SEQ ID NO 51
<211> LENGTH: 5
<212> TYPE: PRT
<213> ORGANISM: Homo sapiens

<400> SEQUENCE: 51

Ser Gly Gly Phe Asn
1               5

<210> SEQ ID NO 52
<211> LENGTH: 5
<212> TYPE: PRT
<213> ORGANISM: Homo sapiens

<400> SEQUENCE: 52

Ser Ser Gly Ser Ser
1               5

<210> SEQ ID NO 53
<211> LENGTH: 50
<212> TYPE: DNA
<213> ORGANISM: Homo sapiens

<400> SEQUENCE: 53
cgacgattga aggtagatac ccatacgacg ttccagacta cgctctgcag         50

<210> SEQ ID NO 54
<211> LENGTH: 50
<212> TYPE: DNA
<213> ORGANISM: Homo sapiens

<400> SEQUENCE: 54
atctcgagct attacaagtc ctcttcagaa ataagctttt gttcggatcc         50

<210> SEQ ID NO 55
```

```
<211> LENGTH: 50
<212> TYPE: DNA
<213> ORGANISM: Homo sapiens

<400> SEQUENCE: 55
gggacctgga agttgttgct gcgaccccca ccagcctact gatcagctgg            50

<210> SEQ ID NO 56
<211> LENGTH: 55
<212> TYPE: DNA
<213> ORGANISM: Homo sapiens

<400> SEQUENCE: 56
tgaactcctg gacagggcta tttcctcctg tttctccgta agtgatcctg taata      55

<210> SEQ ID NO 57
<211> LENGTH: 55
<212> TYPE: DNA
<213> ORGANISM: Homo sapiens

<400> SEQUENCE: 57
caggatcact tacggagaaa caggaggaaa tagccctgtc caggagttca ctgtg      55

<210> SEQ ID NO 58
<211> LENGTH: 53
<212> TYPE: DNA
<213> ORGANISM: Homo sapiens

<400> SEQUENCE: 58
gcatacacag tgatggtata atcaactcca ggtttaaggc cgctgatggt agc        53

<210> SEQ ID NO 59
<211> LENGTH: 53
<212> TYPE: DNA
<213> ORGANISM: Homo sapiens

<400> SEQUENCE: 59
accatcagcg gccttaaacc tggagttgat tataccatca ctgtgtatgc tgt        53

<210> SEQ ID NO 60
<211> LENGTH: 50
<212> TYPE: DNA
<213> ORGANISM: Homo sapiens

<400> SEQUENCE: 60
gatccctggg atggtttgtc aatttctgtt cggtaattaa tggaaattgg            50
```